US008815568B2

(12) United States Patent
Oyler et al.

(10) Patent No.: US 8,815,568 B2
(45) Date of Patent: *Aug. 26, 2014

(54) ENHANCED GENE EXPRESSION IN ALGAE

(71) Applicant: Synaptic Research, LLC, Baltimore, MD (US)

(72) Inventors: George Oyler, Lincoln, NE (US); Julian Rosenberg, Naugatuck, CT (US)

(73) Assignee: Synaptic Research, LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/925,921

(22) Filed: Jun. 25, 2013

(65) Prior Publication Data

US 2013/0273638 A1 Oct. 17, 2013

Related U.S. Application Data

(63) Continuation of application No. 13/504,741, filed as application No. PCT/US2010/055012 on Nov. 1, 2010, now Pat. No. 8,476,019.

(60) Provisional application No. 61/256,921, filed on Oct. 30, 2009.

(51) Int. Cl.
*C12N 1/13* (2006.01)

(52) U.S. Cl.
USPC ............... 435/257.2; 435/320.1; 530/358; 536/23.4; 536/24.1

(58) Field of Classification Search
None
See application file for complete search history.

(56) References Cited

U.S. PATENT DOCUMENTS

| 8,476,019 B2 * | 7/2013 | Oyler et al. ............... 435/6.1 |
| 2003/0145349 A1 | 7/2003 | Odell et al. |
| 2003/0186424 A1 | 10/2003 | Roninson et al. |
| 2006/0003416 A1 | 1/2006 | Otte et al. |

OTHER PUBLICATIONS

Apt et al., Stable nuclear transformation of the diatom *Phaeodactylum tricornutum*, Mol. Gen. Genet. 252:572-579 (1996).
Boise, Lawrence H., et al. "bcl-x, a bcl-2-Related Gene That Functions as a Dominant Regulator of Apoptotic Cell Death." Cell. Aug. 27, 1993. vol. 74. pp. 597-608. Cell Press.
Cadoret et al., Microalgae, Functional Genomics and Biotechnology, Advances in Botanical Research 64:285-342 (2012).
Cerutti, Heriberto, et al. "Epigenetic Silencing of a Foreign Gene in Nuclear Transformants of *Chlamydomonas*." The Plant Cell. Jun. 1997. vol. 9. pp. 925-945. American Society of Plant Physiologists.
Cha, Cinnamic acid, coumarin and vanillin: Alternative phenolic compounds for efficient *Agrobacterium*-mediated transformation of the unicellular green alga, *Nannochloropsis* sp, J. Microbiol. Methods 84:430-434 (2011).
Chen et al., Conditional Production of a Functional Fish Growth Hormone in the Transgenic Line of *Nannochloropsis Oculata* (Eustigmatophyceae), J. Phycol. 44:768-776 (2008).
Chen et al., Highly efficient expression of rabbit neutrophil peptide-1 gene in *Chlorella ellipsoidea* cells, Curr. Genet. 39:365-370 (2001).
Cheng et al., *Agrobacterium tumefaciens* mediated transformation of marine microalgae *Schizochytrium*, Microbiological Research 167:179-186 (2012).
Chow and Tung, Electrotrasnformation of *Chlorella vulgaris*, Plant Cell Reports 18:778-780 (1999).
Coll, J.M., Review. Methodologies for transferring DNA into eukaryotic microalgae, Spanish J. Agric. Res. 4 (4):316-330 (2006).
El-Sheekh, M.M., Stable transformation of the intact cells of *Chlorella kessleri* with high velocity microprojectiles, Biol. Plantarum 42(2):209-216 (1999).
EMBO Practical Course: Molecular Genetics of *Chlamydomonas*. Laboratory Protocols. Geneva, Sep. 18-28, 2006.
Fisher et al., Targeting and Covalent Modification of Cell Wall and Membrane Proteins Heterologously Expressed in the Diatom *Cylindrotheca fusiformis* (Bacillariophyceae), J. Phycol. 35:113-120 (1999).
Franklin, Scott E., et al. "Prospects for molecular farming in the green alga *Chlamydomonas reinhardtii*." Current Opinion in Plant Biology. vol. 7. Apr. 1, 2004 pp. 159-165.
Fukuda, Hiroki, et al. "Simple histone acetylation plays a complex role in the regulation of gene expression." Briefing in Functions Genomics and Proteomics. 2006. vol. 5, No. 3. pp. 190-208. Oxford University Press.
Geng et al., Stable expression of hepatitis B surface antigen gene in *Dunaliella salina* (Chlorophyta), J. Appl. Phycol. 15:451-456 (2003).
Harris, Elizabeth H. "*Chlamydomonas* as a Model Organism." Annu. Rev. Plant Physiol. Plant Mol. Biol. 2001. vol. 52. pp. 363-406. Annual Reviews.
Joung, J. Keith, et al. "A bacterial two-hybrid selection system for studying protein-DNA and protein-protein interactions." Proc. Natnl. Acad. Sci. Jun. 20, 2000. vol. 97., No. 13. pp. 7382-7387.
Kathiresan et al., *Agrobacterium*-Mediated Transformation in the Green Alga *Haematococcus pluvialis* (Chlorophyceae, Volvocales), J. Phycol. 45:642-649 (2009).
Kilian et al., High-efficiency homologous recombination in the oil-producing alga *Nannochloropsis* sp. PNAS 108 (52):21265-21269 (2011).
Kunihiro et al., Development of gene expression system in a marine diatom using viral promoters of a wide variety of origin, Physiol. Plantarum 133:59-67 (2008).
Kwaks, T.H.J., et al. "Targeting of a histone acetyltransferase domain to a promoter enhances protein expression levels in mammalian cells." Journal of Biotechnology. 2002. vol. 115.pp. 35-46.

(Continued)

*Primary Examiner* — Jim Ketter

(74) *Attorney, Agent, or Firm* — Whiteford, Taylor & Preston, LLP; Joseph L. Morales

(57) ABSTRACT

The invention provides eukaryotic unicellular algae engineered to express a nucleosome alteration protein fused to a protein with affinity to the DNA binding site acting in coordination. An example is a LexA-p300 fusion protein, where the p300 is derived from *Chlamydomonas*. The LexA binding domain guides the p300 to the binding site and the p300 loosens the nucleosome structure by acetylating histones within proximity of the transgene, thus remodeling the local chromatin structure to allow for high-level expression.

14 Claims, 4 Drawing Sheets

(56) References Cited

OTHER PUBLICATIONS

Lee, J. H., et al. "Interactions with p300 enhance transcriptional activation by the PDZ-domain coactivator Bridge-1." J. of Endocrinology . 2005. vol. 187. pp. 283-292.

Leon-Banares, R., et al. "Transgenic microalgae as green cell-factories." Trends in Biotechnology. vol. 22, No. 1. Jan. 1, 2004. pp. 45-52.

Lexun et al., Inducible EGFP expression under the control of the nitrate reductase gene promoter in transgenic *Dunaliella salina*, J. Appl. Phycol. 20:137-145 (2008).

Lin, Yu-Yi, et al. "A comprehensive synthetic genetic interaction network governing yeast histone acetylation and deacetylation." Genes & Developments. 2008. vol. 22. pp. 2062-2074. Cold Spring Harbor Laboratory Press.

Lumbreras, Victoria. "Efficient foreign gene expression in *Chlamydomonas reinhardtii* mediated by an endogenous intron." The Plant Journal. 1998. vol. 14, No. 4. pp. 441-447. Blackwell Science Ltd.

Meng et al., Cloning and Characterization of β-Carotene Ketolase Gene Promoter in *Haematococcus pluvialis*, Acta Biochimica et Biophisica Sinica 37(4):270-275 (2005).

Mitra and Higgins, The *Chlorella* virus adenine methyltransferase gene promoter is a strong promoter in plants, Plant Mol. Biol. 26:85-93 (1994).

Miyagawa et al., High efficiency transformation of the diatom *Phaeodactylum tricornutum* with a promoter from the diatom *Cylindrotheca fusiformis*, Phycol. Res. 57:142-146 (2009).

Miyagawa et al., Stable nuclear transformation of the diatom *Chaetoceros* sp., 59:113-119 (2011).

Nagai, Takeharu, et al. "A variant of yellow fluorescent protein with fast and efficient maturation for cell-biological applications." Nature biotechnology. Jan. 2002. vol. 20. pp. 87-90. Nature Publishing Group.

Potvin, Gabriel and Zisheng Zhang. "Strategies for high-level recombinant protein expression in transgenic microalgae: A review." Biotechnology Advances. 2010. pp. 1-9. Elsevier.

Poulsen and Kroger, A new molecular tool for transgenic diatoms. Control of mRNA and protein biosynthesis by an inducible promoter-terminator cassette, FEBS 272:3413-3423 (2005).

Poulsen et al.,Molecular Genetic Manipulation of the Diatom *Thalassiosira pseudonana* (Bacillariophyceae), J. Phycol. 42:1059-1065 (2006).

Rentahl, William and Eric J. Nestler. "Histone acetylation in drug addiction." Seminars in Cell & Development Biology. Jan. 22, 2009. vol. 20. pp. 387-394. Elsevier.

Schrode, Michael, et al. "Sequence elements within a HSP70 promoter counteract transcriptional transgene silencing in *Chlamydomonas*." The Plant Journal. 2002. vol. 31, No. 4. pp. 445-455.

Specht, Elizabeth, et al. "Micro-algae come of age as a platform for recombinant protein production." Biotechnology Letters. vol. 32, No. 10. Jun. 17, 2010.

Steinbrenner and Sandmann, Transformation of the Green Alga *Haematococcus pluvialis* with a Phytoene Desaturase for Accelerated Astaxanthin Biosynthesis, Appl. and Env. Microbiol. 72(12):7477-7484 (2006).

Stevens and Purton, Genetic Engineering of Eukaryotic Algae: Progress and Prospects, Review, J. Phycol. 33:713-722 (1997).

Supplementary European Search Report issued in corresponding European Patent Application No. EP 10 82 7622 on Mar. 15, 2013.

Tan et al., Establishment of a Micro-Particle Bombardment Transformation System for *Dunaliella salina*, J. Microbiol. 43(4):361-365 (2005).

Teng et al., Transient expression of lacZ in bombarded unicellular green alga *Haematococcus pluvialis*, J. Appl. Phycol. 14:495-500 (2002).

Thiel and Poo, Transformation of a Filamentous Cyanobacterium by Electroporation, J. Bacteriol. 171 (10):5743-5746 (1989).

Trichine et al., The Plant Journal, vol. 66 (2011) pp. 45-57.

Walker et al., Algal Transgenics in the Genomic Era, Review, J. Phycol. 41:1077-1093 (2005).

Walker et al., Characterisation of the *Dunaliella tertiolecta* RbcS genes and their promoter activity in *Chlamydomonas reinhardtii*, Plant Cell Reports 23(10-11):727-735 (2004).

Walker et al., Microalgae as bioreactors, Review, Plant Cell Rep. 24:629-641 (2005).

Walker et al., Towards the development of a nuclear transformation system for *Dunaliella tertiolecta*, J. Appl. Phycol. 17:363-368 (2005).

Wang et al., Rapid isolation and functional analysis of promoter sequences of the nitrate reductase gene from *Chlorella ellipsoidea*, J. Appl. Phycol. 16:11-16 (2004).

Waterborg, J.H. "Dynamics of Histone Acetylation in *Chlamydomonas reinhardtii*." Journal of Biological Chemistry. vol. 273, No. 42. Oct. 16, 1998.

Weeks, Donald P., Homologous recombination in *Nannochloropsis*: A powerful tool in an industrially relevant alga, PNAS 108(52):20859-20860 (2011).

Young, K. H. "Yeast Two-Hybrid: So Many Interactions, (in) So Little Time . . . " Biology of Reproduction. 1998. vol. 58. pp. 302-311.

Zaslavskaia et al., Transformation of the Diatom *Phaeodactylum tricornutum* (Bacillariophyceae) with a variety of selectable marker and reporter genes, J. Phycol. 36:379-386 (2000).

\* cited by examiner

ENHANCED GENE EXPRESSION IN ALGAE

CROSS REFERENCE TO RELATED APPLICATIONS

This application is a continuation of U.S. application Ser. No. 13/504,741, entitled "ENHANCED GENE EXPRESSION IN ALGAE" filed Apr. 27, 2012, which issued as U.S. Pat. No. 8,476,019, on Jul. 2, 2013, and which is a national phase of PCT/US2010/055012, entitled "ENHANCED GENE EXPRESSION IN ALGAE" filed Nov. 1, 2010, which claims the priority benefit under 35 U.S.C. §119(e) of U.S. Provisional Application Ser. No. 61/256,921, entitled "ENHANCED GENE EXPRESSION IN ALGAE" filed Oct. 30, 2009, which are both incorporated herein by reference in their entirety.

BACKGROUND OF THE INVENTION

1. Field of the Invention

This invention relates to the field of molecular biology and in particular to the expression of transgenes in algae.

2. Description of the Background

Transgenes are foreign DNA sequences introduced into genomes, in the case of eukaryotic cells within the chromosomes. These genes are usually transcribed as any other gene of the host. Transcription is generally controlled by the chromatin structure that packs the chromosome's DNA into tight bundles in eukaryotic organisms called nucleosomes. As the chromatin structure around a specific gene relaxes, the DNA of the particular gene becomes accessible to the transcription machinery of the cell. Staining indicates that actively transcribed genes in eukaryotes are more loosely incorporated in nucleosomes and more prevalent in euchromatin. In some instances, transgenes are incorporated into the host's chromosome but fail to be expressed due to unfavorable chromatin structures. This phenomenon is called "gene silencing." The ability to control how tightly a nucleosome is packed can help enhance the expression of transgenes in host cells. In mammalian cells, it has been proposed that coupling transgene expression with increased availability of a histone "tail" modifying gene, p300 (also known as a histone acetyl transferase, or "HAT"; in the family of CREB binding proteins, or "CBP"), can increase the expression level, presumably because the acetyl transferase activity causes a looser histone-DNA association and allows transcription factors access to the genes. T. H. J. Kwaks et al., J. Biotechnology, 115:35-46 (2005).

Microalgae encompass a broad range of organisms, mostly unicellular aquatic organisms. The unicellular eukaryotic microalgae (including green algae, diatoms, and brown algae) are photosynthetic and have a nucleus, mitochondria and chloroplasts. The chromatin structure in algae is distinct from other eukaryotes. The chromatin in algae stains heavily, indicating a more compact nucleosome structure and tight association of the DNA to the histones. These differences in chromatin structure of microalgae, particularly in green algae, suggest distinct mechanism of histone chromatin regulation of gene expression.

These differences in eukaryotic microalgae chromatin structure may be the factor behind the observation that stable nuclear transgene expression in microalgae is difficult and transient due to chromatin mediated gene silencing. H. Cerutti, A. M. J., N. W. Gillham, J. E. Boynton, *Epigenetic silencing of a foreign gene in nuclear transformants of Chlamydomonas*, The Plant Cell 9:925-945 (1997). When genetic constructs comprising a mammalian derived anti-apoptotic gene and a fluorescent reporter gene were previously introduced by the present inventors in algae, the expression levels were low and no expression of the fluorescence gene was detected, thus confirming that transgenes are difficult to express in algae.

Algae are considered an important source of healthy nutrients for human consumption and are important as biomass and biofuels. Genetic engineering and stable (over multiple generations) expression of transgenes would open new horizons and greatly enhance the value and desirability to beneficially culture algae. However, as noted above, stable and sufficiently high level of gene expression has been difficult to achieve. A method to improve transgene expression in algae and make that expression stable would be very useful. Such an approach would need to account for the uniquely robust histone mediated gene silencing of microalgae including green algae.

SUMMARY OF THE INVENTION

In accordance with one embodiment, the invention provides a system for enhanced gene expression in algae, the system comprising:

an algae compatible transcriptional promoter functionally upstream of a coding sequence for a gene expression enhancer (GEE) fusion protein, wherein the fusion protein comprises an algae derived p300 functionally fused to the DNA binding protein, wherein at least the portion of the coding sequence of the DNA binding protein domain is codon optimized for improved expression in an algae;

at least one transgene functionally downstream of an algae compatible transcriptional promoter; and at least one DNA region that is a binding site for the DNA binding protein, in vicinity of at least one of said transcriptional promoters;

wherein said system resides in an algae.

In a preferred embodiment, the DNA binding protein is LexA DNA Binding domain. In another preferred embodiment, the p300 part of the GEE fusion protein is from *Chlamydomonas reinhardtii*. In a more preferred embodiment, only a HAT domain of the p300 protein is part of the GEE fusion protein. The p300 or only the HAT domain of p300 may be derived from homologs of other microalgae including green algae in addition to *Chlamydomonas reinhardtii*.

In accordance with another embodiment, the transgene is codon modified for improved expression in algae. In a preferred embodiment, the transgene or gene of interest (GOI) is a fluorescence-Bcl-$x_L$ fusion gene. The fusion protein may include a fluorescence-Bcl-$x_L$ construct (e.g. YFP-Bcl-$x_L$ fusion or a Venus-Bcl-$x_L$ fusion). In another preferred embodiment, the transgene is the YFP/Venus gene, not necessarily part of a fusion protein. Venus is an enhanced yellow fluorescent protein (YFP) that is stable over a wide range of pH, folds quickly, and emits at 30-fold the intensity of conventional YFP. Nagai T., Ibata K., Park E. S., Kubota M., Mikoshiba K. and Miyawaki A. (2002). A variant of yellow fluorescent protein with fast and efficient maturation for cell-biological applications. *Nature Biotechnol*, 20, 87-90.

In accordance with another embodiment, the system further comprises at least one selective marker such as an antibiotic resistance marker. In a preferred embodiment, the GEE fusion protein and the at least one transgene are introduced into the system on one vector and structurally arranged to be expressed from one bidirectional promoter region and comprising DNA binding sites in the vicinity of both promoters.

In a more preferred embodiment, the GEE fusion protein and the transgene are introduced in the system on separate vectors, each comprising a selective marker and the selective markers are not the same. When separate vectors, both the GEE vector and the vector for the gene of interest (GOI) will contain selective markers. When the GEE is introduced on a separate vector from the vector for the GOI, the GEE vector may be used to generate a stable algae cell line that will serve as the recipient for the second vector expressing the GOI. This stable GEE algae cell line will function to enhance the expression of the second vector containing the GOI.

In accordance to yet another embodiment, the algae compatible transcriptional promoters are hsp70, rbcS, nitA, actin, tubA2 or a combination thereof.

In accordance to another yet embodiment, the GEE fusion protein comprises a DNA binding domain functionally fused to an algae derived p300 homologue having at least 80% identity over the HAT region to the p300 from *Chlamydomonas reinhardtii*. Preferably, the GEE fusion protein comprises a DNA binding domain functionally fused to the HAT domain of the HAT region to the p300 from *Chlamydomonas reinhardtii*. It is noteworthy that the p300 from mammalian species is much larger in size and is much less that 50% similar to *Chlamydomonas reinhardtii* p300.

The invention also provides a method of expressing a gene in algae at higher levels, comprising:

transforming algae with at least one vector comprising:

an algae compatible transcriptional promoter functionally upstream of a coding sequence for a gene expression enhancer (GEE) fusion protein, wherein the fusion protein comprises an algae derived p300 functionally fused to the DNA binding protein, wherein at least the portion of the coding sequence of the DNA binding protein domain is codon optimized for improved expression in an algae;

at least one transgene functionally downstream of an algae compatible transcriptional promoter; and at least one DNA region that is a binding site for the DNA binding protein, in vicinity of at least one of said transcriptional promoters;

selecting a transformed algae cell; and detecting the expression of said GEE gene and/or said transgene in algae.

In a preferred embodiment, the DNA Binding protein is the LexA binding domain, and more preferably the p300 is from *Chlamydomonas reinhardtii*. More preferably yet, the GEE fusion protein comprises the LexA binding domain functionally fused with the HAT domain of the p300 protein from *Chlamydomonas reinhardtii*.

In accordance to another embodiment, the transgene is a YFP-Bcl-$x_L$ fusion protein or a Venus-Bcl-$x_L$ fusion protein.

In accordance to yet another embodiment, the GEE fusion protein and said transgene are transformed in algae on separate vectors, first selecting a vector stably expressing the GEE fusion protein and then transforming the selected algae with the vector comprising the transgene.

BRIEF DESCRIPTION OF THE DRAWINGS

FIG. 2A is a vector expressing a LexA-p300 fusion protein. FIG. 2B illustrates a vector expressing another gene which is advantageously introduced in algae ("gene of interest or "GOI"). In accordance to this embodiment, each of the LexA-p300 fusion and the GOI have, at or near their 5'-ends, LexA binding site(s).

DETAILED DESCRIPTION

Figure 1:
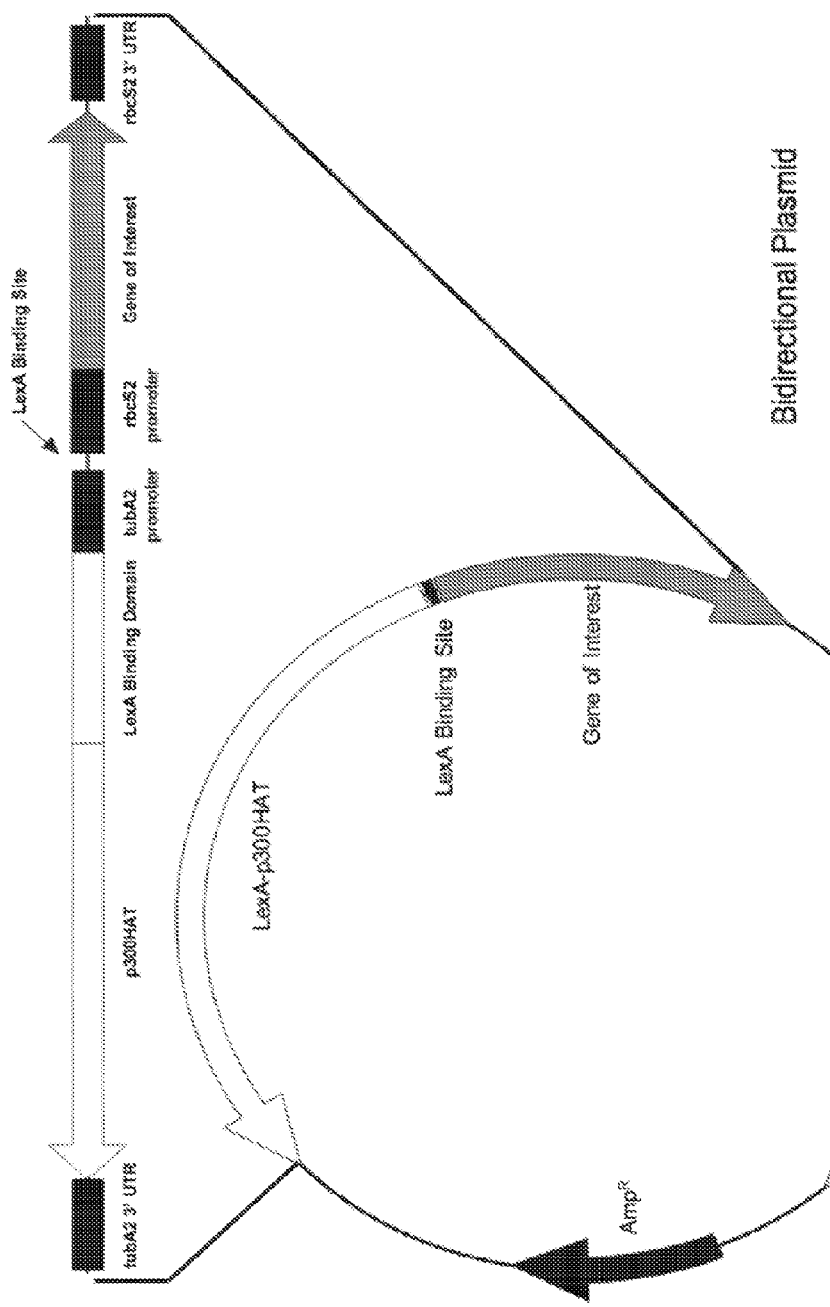
FIG. 1 illustrates the features of a vector in accordance to one embodiment of the present invention. The direction of transcription is indicated by arrows. The figure indicates certain structural components, as discussed herein elsewhere. The linear drawing provides further details of the respective region of the vector: a fused LexA-p300 protein coding region and a coding region of a GOI. In this embodiment, these two coding regions are transcribed in opposite directions (thus the "bidirectional" nomenclature). These two coding regions are separated by a locus comprising LexA binding sites.

Expression of transgenes in the algae is difficult. H. Cerutti, A.M.J. et al., The Plant Cell 9:925-945 (1997). Likewise, when the present inventors transformed a microalgae with a construct expressing a yellow florescence protein ("YFP") fused to a cancer suppressing Bcl-$x_L$ gene (the transcription driven by the rubisco promoter (rcbS2) and relying on a heat shock translational enhancer (HSP70)), the transformed microalgae failed to produce fluorescence. However, transformants which survived marginally longer and were morphological affected (the result of limited expression of the Bcl-$x_L$ gene) were observed. It is expected that that gene silencing contributed to the poor expression of the transgenes in algae.

The present invention provides an effective method to increase transgene expression in algae, preferably a green algae, more preferably a microalgae. A preferred algae of the invention is an unicellular, photosynthetic algae. A yet more preferred algae is the microalgae. The GOI transgene expressed in the algae in accordance to the invention is expressed to a higher level. The expression is increased by at least 50%, preferably about two to at least five fold, relative to the expression of the same transgene engineered in the algae without the benefit of the present invention. In respect of fluorescence transgenes, the expression is increased sufficiently to allow monitoring the fluorescence signal. More preferably, the fluorescence signal is monitored in *Chlamydomonas*.

The transgene is introduced in algae. In accordance with an embodiment of the present invention, the transgene is placed on a vector. The vector is a nucleic acid structure used to introduce a cassette containing a DNA sequence into an algae chromosome. The vector is introduced in the nucleus of a host algae cell and the transgene is transcribed/translated in the algae. Methods of transformation of algae are well known to artisans skilled in the art. For example, a vector construct may be introduced via electroporation, via plasmid conjugation, and via particle bombardment. The transformed algae are recovered on a solid nutrient media or in liquid media. Elizabeth H Harris, *Chlamydomonas As A Model Organism*, Annual Review of Plant Physiology and Plant Molecular Biology 52:363-406 (2001) and EMBO Practical Course:

Molecular Genetics of *Chlamydomonas*, Laboratory protocols. Geneva, Sep. 18-28, 2006.

A preferred vector of the invention is a plasmid capable of integrating the DNA sequence of interest into a chromosome of the algae. There are a large numbers of vectors known and characterized. A preferred vector of the invention is pSP124. Lumbreras et al., Efficient foreign gene expression in *Chlamydomonas reinhardtii* mediated by an endogenous introns, The Plant Journal 14(4):441-447 (1998).

Methods of engineering vectors are well known in the art. The vector backbone may include genes encoding transformation markers, to indicate transformation of the host cell with the vector. A transformation marker may be a selective marker gene used to select cells in which the vector is present from normal cells without the vector. Selective markers are well known to artisans skilled in the art. Commonly used selective markers include genes that confer resistance to specific antibiotics such as bleomycin. Only cells containing the vector grow in media containing the antibiotic. Other vector backbones may also include marker genes that merely indicate which cells were transformed. When such markers are used, cells with and without the vector will grow but the cells containing the vector can be distinguished from those not having the vector because they display a specific characteristic conferred by the vector, e.g., color. A commonly used transformation marker gene is the yellow or green fluorescence gene. Cells containing a vector with such a gene will be yellow or green. Other common transformation markers include various luciferase genes. Cells containing the luciferase genes emit light.

Any effective combination of gene expression regulatory features compatible with expression of genes in the algae nucleus can be incorporated in the vector. The plasmid may include different types of promoters, for example constitutive promoters or inducible promoters. Preferred transcriptional promoters in accordance to the invention include the hsp70 ("heat shock protein" promoter), rbcS ("rubisco small subunit" promoter) and tubA2 ("actin" promoter). The vector employs suitable translational enhancer elements, generally referred to as 5'untranslated regions or "5'UTR." Preferred enhancers in accordance to the invention are the tubA2 intron 1, the HSP70 enhancer, and the rcbS2 intron 1. The vector of the invention includes also effective translational terminators, 3'UTR. Examples of preferred 3'-UTR sequences include the tubA2, HSP70, and rcbS2 3'UTR. Other effective promoters, transcription enhancers and terminators may, in particular combinations, may produce satisfactorily high and stable expression.

Figure 2A:
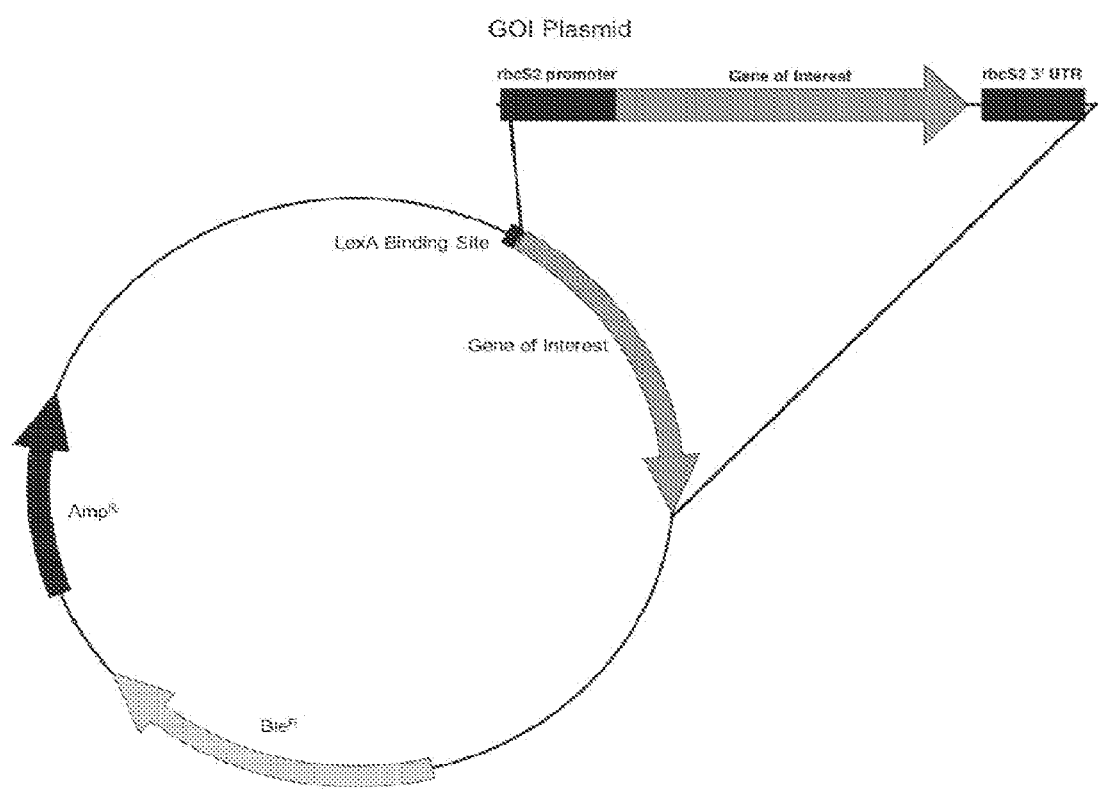
FIGS. 2A and 2B illustrate another embodiment of the invention.

Some of these options are illustrated in FIGS. 1 and 2. The features selected to be exemplified in FIGS. 1 and 2 include the promoter and 3'UTR regions of the Chlamy genes: tubA2 encoding actin (Tubulin); rbcS2 encoding the rubisco small subunit; or nitA encoding nitrate reductase. Furthermore, the hsp70A/rbcS2 tandem promoter is a preferred driver of transgene expression. Schroda M., Beck C. F. and Vallon A., Sequence elements within an hsp70 promoter counteract transcriptional transgene silencing in *Chlamydomonas*. Plant J. 31:445-455 (2002). This chimeric promoter contains the enhancer region of the nucleo-cytoplasmic-localized 70 kD heat shock protein gene (NCBI GenBank ID: M76725; by 572-833) and the promoter from the nuclear rubisco small subunit gene (NBCI GenBank ID: X04472; bp 934-1142). Additionally, the first intron (bp 1307-1451) and 3'-untranslated region (bp 2401-2632) of the rbcS2 gene may be included to further promote stable transgene expression.

In accordance with an embodiment of the present invention, one or more vectors are used to introduce a cassette that contains a gene of interest ("GOI") and a gene silencing inhibitor into the nucleus DNA of algae, e.g., a Chlamy nucleus. The GOI can be any gene desirably expressed in algae. Viable genes of interest include genes involved in controlling algae's metabolic pathways. For example, in one embodiment of the present invention the Bcl-$x_L$ gene can be inserted and expressed in the algae's nucleus. Bcl-$x_L$ is an abbreviation for B-cell lymphoma extra-large; it is known to be an inhibitor of apoptosis (programmed cell death). Boise L. H. et al., *Bcl-x, a bcl-2-related Gene that Functions as a Dominant Regulator of Apoptotic Cell Death*, Cell 74:597-608 (1993). In another embodiment genes affecting lipid or isoprenoid production pathways are desirably introduced. Due to Bcl-$x_L$'s ability to inhibit apoptosis, its expression allows algae cells to live longer. A longer lifespan for microalgae enables the use of microalgae in various industrial applications such as photobioreactors.

A gene silencing inhibitor is also introduced into the algae. A gene silencing inhibitor is a peptide that induces relaxation of nucleosomes in the algae's nucleus. Gene silencing inhibitors include histone acetyl transferases (HATs) and other peptides that modify elements of the nucleosome, causing the chromatin structure to relax and to allow transcription factors to access the gene of interest. HAT proteins and the HAT domains of p300 and of other HAT proteins are known to cause histone acetylation and can be utilized in the invention. In accordance to the invention the domain responsible for the acetylation activity or the whole protein is deployed. See Fukuda H, et al., Brief Funct. Genomic Proteomic, 5(3):190-208 (2006); Renthal W. and Nestler E. J., Semin Cell Dev Biol. 20(4):387-94 (Epub 2009); and Lin Y. Y. et al., Genes Dev., 22(15):2062-74 (2008).

One preferred embodiment of the present invention utilizes a p300 protein as a gene silencing inhibitor. More preferably, a Chlamy derived p300 protein is utilized. In a yet more preferred embodiment, the Chlamy p300 protein is the homologue detailed in FIG. 3. In a further more preferred embodiment, only the HAT domain of the Chlamy p300 gene is utilized. See FIG. 3 and relevant portion of SEQ ID NO 4.

Figure 3:
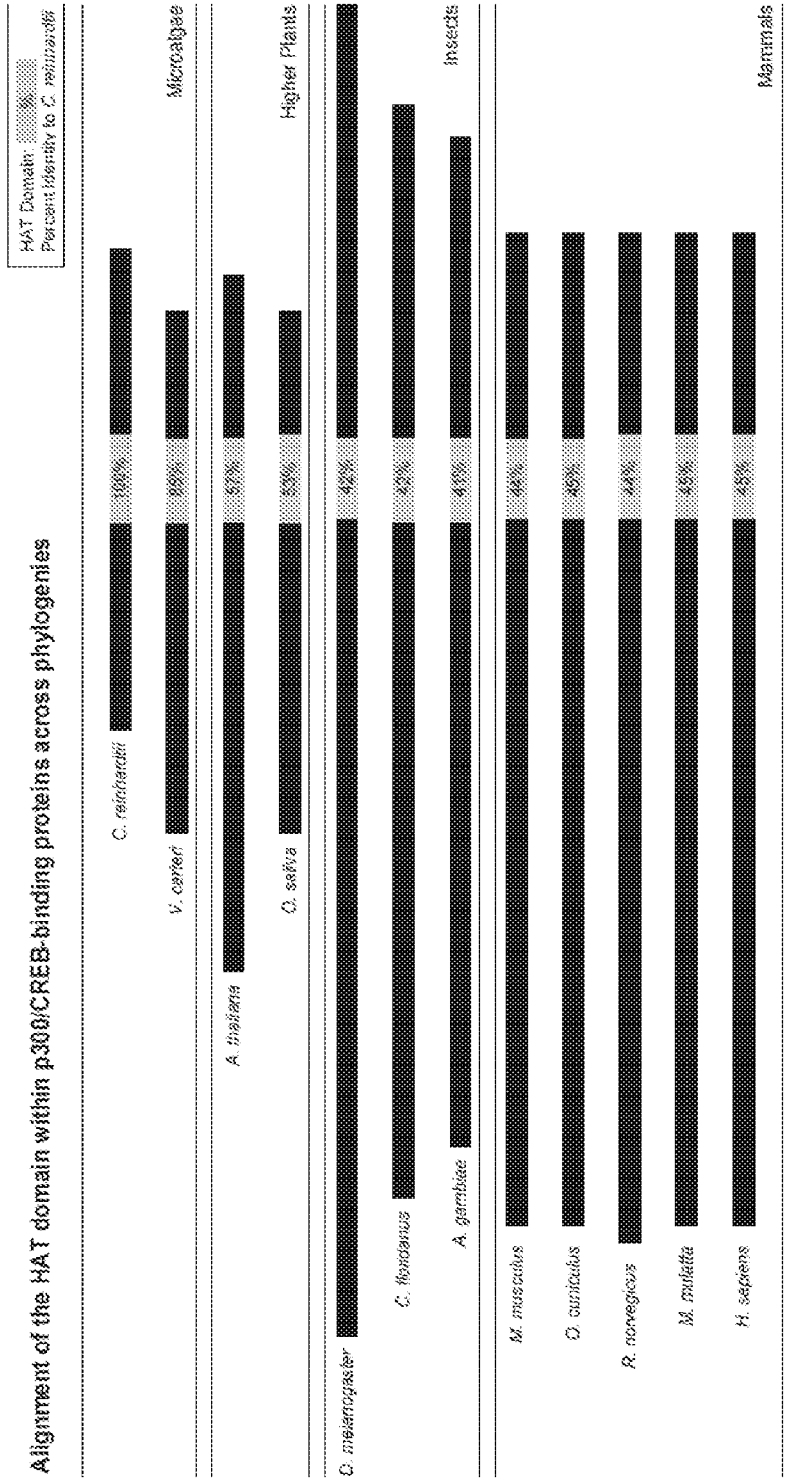
FIG. 3 compares the putative p300 protein from algae (*Chlamydomonas reinhardtii* ("Chlamy") with known p300 proteins from the indicated phylogenetically representative species. The lighter colored section of each bar represents the histone acetylase (HAT) domain. The HAT domains are aligned for visualization purposes. These lighter bars include numbers that are indicative of the percent identity of the HAT domain of each protein proteins within each panel, with the indicated percentages of identity of each HAT protein to the p300 HAT domain of the p300 protein from Chlamy. The figure is drawn to scale, both in respect to the overall size of the p300 proteins and the location of the HAT domain within the protein.

FIG. 3 shows an alignment comparison of the Chlamy p300 with phylogenetically distinct other p300 homologues. The lighter colored section of each bar represents the histone acetylase (HAT) domain. The HAT domains are aligned for visualization purposes. These lighter bars include numbers that are indicative of the percent identity of the HAT domain of each protein proteins with the indicated percentages of identity of each HAT protein to the p300 HAT domain of the p300 protein from Chlamy. FIG. 3 is drawn to scale, both in respect to the overall size of the p300 proteins and the location of the HAT domain within the protein.

Table 1, exemplifies the highly conserved nature of the p300 proteins and particularly conserved nature of the HAT domains.

TABLE 1

Comparison of HAT domain identity within each phylogenetic clade.

| C. reinhardtii - 100% | A. thaliana - 100% | D. melanogaster - 100% | H. sapiens - 100% |
|---|---|---|---|
| V. carteri - 85% | G. max - 91% | A. gambiae - 92% | M. mulatta - 100% |
| | O. sativa - 91% | C. floridanus - 89% | O. cuniculus - 100% |
| | S. bicolor - 90% | | R. norvegicus - 99% |
| | P. trichocarpa - 88% | | H. musculus - 99% |
| Microalgae | Higher Plants | Insects | Mammals |

The bolded organism at the top of each column is the representative species to which all other percent identities are based.

Indeed, the percent identity between plant and mammalian p300 homologues is also very high, typically at least about 80%. See US Patent Publication US2003/0145349. However, the homology of the Chlamy p300 homologue to other organisms is lower. Likewise, the p300 full protein of *Chlamydomonas reinhardtii* is 11.5% identical and further 9.9% similar to the mouse p300 protein; 9.1% identical and a further 4.7% similar to the *Drosophila* p300 protein; and 23.6% identical and a further 9.9% similar to the *Arabidopsis* p300 protein. The Chlamy derived protein has N-terminal or C-terminal regions which are shorter and dissimilar in their location visa-vie the HAT domain to these of the mammalian or plant p300 proteins. See FIG. 3. This is suggestive of proteins with overall distinct functions and phylogeny.

The various proteins p300 homologues in FIG. 1 and described herein elsewhere are:

- *C. reinhardtii* p300/HAT Protein ID: 159467703 from NCBI Database.
- *V. carteri* p300/CBP Protein ID: 300256266 from NCBI Database.
- *S. bicolor* putative p300 Protein ID: C5XTZ4 from Universal Protein Resource.
- *P. trichocarpa* GenBank ID: POPTR_007s15090 from Joint Genome Institute Database.
- *G. max* Protein ID: PF02135 from Joint Genome Institute Database.
- *A. thaliana* HAC1/p300/CBP GenBank ID: NM_106550.3 from NCBI Database.
- *O. saliva* p300/CBP Protein ID: 108792657 from NCBI Database.
- *D. melanogaster* CBP/HAT Genbank ID: NM_079903.2 from NCBI Database.
- *A. gambiae* HAT Protein ID: 158289391 from NCBI Database.
- *C. floridanus* CBP Protein ID: 307172990 from NCBI Database.
- *M. musculus* E1A/BP/p300 GenBank ID: NM_177821.6 from NCBI Database.
- *O. cuniculus* p300 Protein ID: 291410334 from NCBI Database.
- *R. norvegicus* p300 Protein ID: XP_576312.3 from NCBI Database.
- *M. mulatta* p300 HAT Protein ID: XP_001102844.1 from NCBI Database.
- *H. sapiens* p300 Protein ID: NP_001420.2 from NCBI Database.

In another preferred embodiment of the present invention, the gene silencing inhibitor is functionally tethered or, preferably, fused to a DNA binding protein or domain thereof (the tethered/fused protein or its/their gene hereinafter are referred to as the gene expression enhancer unit, or "GEE"). The DNA binding protein or domain binds to a particular DNA sequence (Binding Site or "BS"), bringing the gene silencing inhibitor to its histone target at a location in the vicinity of the BS and thereby inducing relaxation of the nucleosome at that genetic location. As the nucleosome relaxes, the nearby DNA sequence is exposed to transcription factors and is more actively transcribed.

In accordance to a preferred embodiment, the invention requires the expression in an algae protein that binds specific DNA sequences, which sequences can be engineered upstream of any GOI for expression in algae. The DNA binding protein/domain can be any protein having known DNA binding sites can be used. Examples of proteins targeting specific DNA motifs applicable to this invention include the Gal4 protein and Early Growth Response Protein 1. DNA binding site motifs for these proteins are known. Likewise, the binding domains of these as well as the LexA protein are known and are preferentially used, instead of the full-length protein. See for example Young, K., Biol. Reprod., 58:302-311 (1998) and Joung, J. et al., Proc. Natnl. Acad. Sci., 97:7382-7 (2000). The DNA binding site (BS) for Gal4 is 5'-CGGAGGACAGTCCTCCG-3' (SEQ ID NO 10).

LexA is a preferred example of a DNA binding protein. LexA is a gene of bacterial origin. LexA proteins or genes are not known in algae. Thus, it is unlikely that the Chlamy genome will contain the DNA binding sequence of LexA. The function of LexA in the context of the invention is to bind a particular DNA sequence (binding site, "BS"). LexA binding sites are found upstream promoters in a number of microorganisms. A consensus BS sequence for LexA is CTG-TATATATATACAG. SEQ ID NO 9. The binding domain of the LexA protein is known and, for the purpose of the invention, it is preferred to employ only the binding domain. Protein ID: 2293118 from NCBI Database: MKALTAR-QQEVFDLIRDHISQTGMP PTRAEIAQRLGFRSPNAAEEHLKA-LARKGVIEIVSGASRGIRLLQEEEEGLPLVGRVAAG EPLLAQQHIEGHYQVDPSLFKPNADFLL-RVSGMSMKDIGIMDGDLLAVHKTQDVRNGQ VVVARIDDEVTVKRLKKQGNKVELL-PENSEFKPIVVDLRQQSFTIEGLAVGVIRNGDWL EFP-GIRRPWRPLESTCSQANSGRISYDL (SEQ ID NO 11).

As noted above, the DNA binding protein or domain thereof, preferably the LexA domain, is constructed to translate in a protein allowing the DNA binding domain and a nucleosome relaxation protein to act in concert. Any nucleosome relaxation protein might be used. Preferably, as noted above, a Chlamy p300 domain is used.

Without being limited to a single mechanism of action, it is proposed that one partner binds to the DNA, the other acetylates nearby histones, thereby creating a looser association between the DNA and the histones at that site. Therefore any method to render the DNA binding domain and the acetylase domain spatially close to each other is preferred. A fused protein is more preferred. The order of the two units (N-terminal proximity) within the fusion protein is not critical. However, in the p300-LexA binding domain example, it is preferred that LexA binding domain is at the N-terminal end of the fusion. "Functional" fusion proteins are designed. By way of example, certain linker regions are introduced to allow flexibility, orientation or simply "dead" protein sequence corresponding to strategically placed genetic engineering features such as primers and restriction enzyme sites.

Preferably, the GEE can be a p300 peptide homolog and the DNA binding domain can be LexA binding domain, creating a p300-LexA binding domain fusion protein and its gene construct. Preferably, that fusion is an algae p300-LexA binding domain fusion. More preferably, the fusion is the Chlamy p300-LexA fusion. Alternatively, the fusion comprises select domains of the Chlamy p300-LexA proteins. See SEQ ID NO 4. Yet more preferably, the fusion, at the nucleic acid level, comprises a LexA sequence modified in its codon usage for higher yield when expressed in algae. Preferably, the whole of the GEE fusion protein gene was designed for preferred codon usage in algae, even if part of the gene (p300) is an algae derived gene, as provided by SEQ ID NO 1 and SEQ ID NO 3. Indeed, the transgene (GOI) and other genes in the system preferably are codon optimized based on codon frequency in algae.

It should be noted that other algae p300 homologues or their acetylasehistone acetyltransferase (HAT) domains may be preferentially used in the invention. However, these preferred homologues must be at least about 60% identical to the Chlamy p300, preferably at least about 70% identical, at least about 80% identical, at least about 85% identical, at least about 90% identical or more. A p300 homologue from *V. carteri* (algae) was recently identified. It has about 85% identity to the Chlamy p300, over the HAT domains.

The LexA-p300 fusion DNA (SEQ ID 1) is the nucleotide sequence encoding a fusion protein (exemplary GEE) comprising the LexA binding domain and the full length Chlamy p300 sequence, all of the fusion designed to reflect preferred codon usage in algae. It was adapted to the nuclear codon usage of *C. reinhardtii* according to the table provided by the Kazusa Codon Usage Database (Species ID: 3055), using Gene Designer software from DNA 20. The sequence up to nucleotide 690 is that of the LexA DNA binding domain and the fell length *C. reinhardtii* p300 sequence begins at nucleotide 700. A 3-amino acid peptide linker (GVL) connects LexA binding domain and p300, which represents the DNA restriction site PpuMI (9 bp). The LexA gene sequence is codon-optimized for *C. reinhardtii* nuclear expression using AA sequence from Protein ID: 2293118 from NCBI Database:

```
                                                               SEQ ID NO 1
   1    ATGAAGGCTCTGACCGCTCGCCAGCAGGAGGTGTTTGATCTGATTCGGGA

51    CCATATCAGCCAAACGGGCATGCCCCCTACGCGCGCGGAGATCGCGCAAC

101    GGCTGGGCTTCCGCTCCCCGAACGCGGCTGAGGAGCACCTGAAGGCGCTG

151    GCGCGCAAGGGTGTGATTGAGATCGTCTCCGGCGCGTCGCGGGGCATTCG

201    GCTGCTGCAGGAGGAGGAGGAGGGTCTGCCTCTGGTGGGGCGGGTGGCTG

251    CGGGCGAGCCCCTGCTGGCCCAGCAGCACATTGAGGGCCACTACCAAGTG

301    GACCCGTCCCTCTTCAAGCCGAACGCCGATTTCCTGCTGCGCGTCAGCGG

351    TATGAGCATGAAGGACATCGGCATCATGGACGGTGACCTGCTGGCCGTGC

401    ATAAGACGCAGGACGTGCGCAACGGCCAAGTGGTCGTCGCCCGCATCGAT

451    GACGAGGTGACCGTGAAGCGCCTGAAGAAGCAGGGGAACAAGGTCGAGCT

501    GCTGCCCGAGAACAGCGAGTTCAAGCCCATCGTGGTGGATCTGCGCCAGC

551    AATCCTTCACCATCGAGGGCCTGGCGGTGGGCGTGATCCGCAACGGCGAC

601    TGGCTGGAGTTCCCGGGCATCCGCCGCCCGTGGCGCCCTCTGGAGTCCAC

651    GTGCTCGCAGGCCAACTCCGGCCGCATTAGCTACGACCTGGGGGTCCTTA

701    TGGTGCCGATGGGCGCGCCCGCTATGCCCATGGGCAACAACGGCTCGCCC

751    ATGCTGAACGGCATGGGTATGTTCAACGCCCCGCAGCAGACCGTGCCCAA

801    CGGCGGGCCGGGTGGCGTGAACCCCATGGGCCAGGTGCCGGCGATGCCTG

851    CGCCGATCCCCAACGGCGGTCTGCCCGGTATGAACGCTGCCGGCGGTGCC

901    GACGATCCTGCGAAGCAGCGGGAGCAATCGATCCAGAAGCAGCAGCGCTG

951    GCTGCTGTTCCTGCGGCACTGCGCGAAGTGCCGGGCTCCCGGCGAGGACT

1001    GCCAGCTGAAGTCCCAGTGCAAGTTCGGCAAGCAGCTGTGGCAGCACATC

1051    CTGTCGTGCCAAAACCCGGCCTGCGAGTACCCGCGCTGCACCAACTCCAA

1101    GGATCTGCTCAAGCACCACCAGAAGTGCCAGGAGCAGACCTGCCCCGTGT

1151    GCATGCCGGTGAAGGACTACGTGAAGAAGACGCGCCAGGCGACCCAACAG

1201    CAGCAACAAATGCAGCAACAACAGCAAATCCAGCAACAGCAACAACAACA
```

-continued

```
1251 AATGCAACAGCAACAGATGCAACAGCAGCAGCTCCAGCAGCAGCAGATGC

1301 AACAACAACAGCAGATGCAGCAGCAGCAACAGCCCGGCGTGGGCGCCAAC

1351 TTCATGCCCACCCCGCCCATGATGCCGAACGGCATGTTCCCTCAACAGCA

1401 GCCCCAGCAGGCGATGCGCCTGAACGCCAACGGCCTCGGCGGCCAGAAGC

1451 GCCCCCACGAGATGATGGGTATGTCCAGCGGCGGCATGGACGGTATGAAC

1501 CAGATGGTGCCCGTCGGCGGCGGCGGCATGGGCATGTCGATGCCGATGGG

1551 TATGAACAACCCCATGCAGGGCGGTATGCCCCTGCAGCCTCCGCCCCAGG

1601 TGCAGGCTCCCGGTCAGGGCCCCATGATGAGCGCCCCTCAGCAGCAACAG

1651 CAGCAACCGGCCCCTAAGCGGGCGAAGACCGACGATGTGCTGCGCCAGAA

1701 CACGGGCACCAGCCTCCTGGAGACGTTCGACGCCAAGCAGATCCGCGTGC

1751 ACGTGGACCTGATCCGCGCTGCCGCGGTGACCCAGAAGGCCCAGCAGCCT

1801 CCCCCGGCTAACCCCGACGACGCGTGCAAGGTCTGCGCGCTGACGAAGCT

1851 GTCGTTCGAGCCCCCGGTGATTTACTGCTCGAGCTGCGGCCTGCGCATCA

1901 AGCGCGGCCAGATCTTCTACAGCACGCCTCCGGACCACGGCAACGACCTG

1951 AAGGGTTACTTCTGCCACCAGTGCTTCACCGACCAGAAGGGCGAGCGCAT

2001 CCTGGTGGAGGGCGTCTCGATCAAGAAGAGCGACCTGGTGAAGCGCAAGA

2051 ACGATGAGGAGATCGAGGAGGGGTGGGTGCAGTGCGACCACTGCGAGGGC

2101 TGGGTGCACCAGATTTGCGGCATGTTCAACAAGGGCCGGAACAACACGGA

2151 CGTCCACTACCTGTGCCCTGACTGCCTGGCCGTGGGCTACGAGCGCGGCC

2201 AGCGCCAGAAGACGGAGGTCCGCCCCCAGGCGATGCTCGAGGCGAAGGAT

2251 CTGCCCACGTCCCGGCTGTCCGAGTTTATTACGGAGCGCCTGAACCGCGA

2301 GCTGGAGAAGGAGCACCACAAGCGGGCTGAGCAGCAGGGCAAGCCGCTGC

2351 ACGAGGTGGCGAAGCCCGAGCCCCTGACCGTGCGGATGATCAACTCCGTG

2401 ATGAAGAAGTGCGAGGTCAAGCCGCGCTTCCACGAGACGTTCGGCCCCAC

2451 CGACGGCTACCCCGGGGAGTTCGGCTACCGGCAGAAGGTGCTGCTGCTGT

2501 TCCAAAGCCTGGACGGTGTCGACGTGTGCCTGTTCTGCATGTACGTGCAG

2551 GAGTACGGCAAGGACTGCCCTGCGCCCAACACCAACGTGGTGTACCTGTC

2601 GTATCTGGACTCCGTCAAGTACTTCCGCCCTGAGATTCCCTCGGCCCTGG

2651 GCCCTGCCGTGTCGCTGCGCACCTTCGTGTACCACCAACTCCTGATCGCC

2701 TACGTGGAGTTTACCCGCAACATGGGTTTTGAGCAGATGTACATTTGGGC

2751 GTGCCCGCCGATGCAAGGCGACGACTACATCCTGTACTGCCACCCGACCA

2801 AGCAGAAGACGCCGCGCTCGGACCGCCTGCGCATGTGGTACATTGAGATG

2851 CTGAAGCTGGCGAAGGAGGAGGGTATCGTGAAGCACCTGAGCACGCTGTG

2901 GGATACGTACTTCGAGGGCGGTCGCGACCACCGGATGGAGCGCTGCTCGG

2951 TCACGTACATTCCGTACATGGAGGGCGACTACTGGCCCGGCGAGGCTGAG

3001 AACCAGCTCATGGCCATTAACGACGCGGCCAAGGGCAAGCCTGGGACCAA

3051 GGGTGCGGGCAGCGCCCCGAGCCGCAAGGCCGGTGCCAAGGGCAAGCGCT

3101 ACGGCGGTGGCCCCGCCACGGCTGATGAGCAGCTGATGGCCCGCCTCGGT

3151 GAGATCCTGGGCGGGAACATGCGGGAGGACTTCATTGTGGTCCACATGCA

3201 GGTGCCCTGCACGTTCTGCCGCGCTCACATTCGGGGTCCGAACGTGGTGT
```

```
3251  ACCGCTATCGGACGCCGCCTGGCGCGACCCCTCCCAAGGCTGCCCCCGAG
3301  CGCAAGTTCGAGGGCATCAAGCTGGAGGGCGGTGGCCCCAGCGTGCCCGT
3351  GGGCACCGTCTCGAGCCTGACGATCTGCGAGGCGTGCTTTCGCGACGAGG
3401  AGACGCGCACGCTGACCGGCCAACAGCTGCGCCTGCCCGCTGGCGTGTCG
3451  ACCGCTGAGCTCGCGATGGAGAAGCTGGAGGAGATGATCCAGTGGGACCG
3501  CGACCCTGACGGCGACATGGAGAGCGAGTTCTTCGAGACGCGGCAGACCT
3551  TCCTGTCGCTGTGCCAGGGCAACCACTACCAGTTCGACACCCTCCGCCGC
3601  GCTAAGCACTCGTCGATGATGGTGCTCTACCACCTGCACAACCCCCACTC
3651  GCCGGCGTTCGCGTCCTCGTGCAACCAGTGCAACGCCGAGATCGAGCCGG
3701  GCAGCGGCTTTCGCTGCACCGTGTGCCCCGACTTCGACATGTGCGCCAGC
3751  TGCAAGGTCAACCCTCATAAGCGCGCCCTGGACGAGACGCGCCAGCGGCT
3801  GACCGAGGCCGAGCGCCGGGAGCGCAACGAGCAGCTGCAGAAGACCCTCG
3851  CCCTGCTGGTGCACGCCTGCGGCTGCCACAACAGCGCGTGCGGCTCCAAC
3901  AGCTGCCGCAAGGTGAAGCAGCTGTTCCAGCACGCGGTCCACTGCCAGAG
3951  CAAGGTGACCGGGGGCTGCCAGCTGTGCAAGAAGATGTGGTGCCTGCTGA
4001  ACCTGCACGCCAAGTCCTGCACCCGCGCGGACTGCCCGGTGCCGCGCTGC
4051  AAGGAGCTGAAGGAGCTGCGCCGGCGCCAAACGAACCGGCAGGAGGAGAA
4101  GCGCCGGGCGGCCTACGCCGCTATGCTGCGCAACCAGATGGCCGGCAGCC
4151  AGGCTCCGCGCCCCATGTAA.
```

LexA-p300 Fusion Protein (SEQ ID NO 2) is the respective protein sequence encoded by the nucleic acid sequence of SEQ ID NO 1. The LexA binding domain is the sequence up to and including amino acid 230 and the full-length p300 HAT domain sequence begins at amino acid 234. A 3-amino acid peptide linker (GVL) connects LexA binding domain and p300, which represents the DNA restriction site PpuMI (9 bp):

```
                                              SEQ ID NO 2
  1  MKALTARQQEVFDLIRDHISQTGMPPTRAEIAQRLGFRSPNAAEEHLKAL
 51  ARKGVIEIVSGASRGIRLLQEEEEGLPLVGRVAAGEPLLAQQHIEGHYQV
101  DPSLFKPNADFLLRVSGMSMKDIGIMDGDLLAVHKTQDVRNGQVVVARID
151  DEVTVKRLKKQGNKVELLPENSEFKPIVVDLRQQSFTIEGLAVGVIRNGD
201  WLEFPGIRRPWRPLESTCSQANSGRISYDLGVLMVPMGAPAMPMGNNGSP
251  MLNGMGMFNAPQQTVPNGGPGGVNPMGQVPAMPAPIPNGGLPGMNAAGGA
301  DDPAKQREQSIQKQQRWLLFLRHCAKCRAPGEDCQLKSQCKFGKQLWQHI
351  LSCQNPACEYPRCTNSKDLLKHHQKCQEQTCPVCMPVKDYVKKTRQATQQ
401  QQQMQQQQQIQQQQQQQMQQQQMQQQQLQQQQMQQQQQMQQQQQPGVGAN
451  FMPTPPMMPNGMFPQQQPQQAMRLNANGLGGQKRPHEMMGMSSGGMDGMN
501  QMVPVGGGMGMSMPMGMNNPMQGGMPLQPPPQVQAPGQGPMMSAPQQQQ
551  QQPAPKRAKTDDVLRQNTGTSLLETFDAKQIRVHVDLIRAAAVTQKAQQP
601  PPANPDDACKVCALTKLSFEPPVIYCSSCGLRIKRGQIFYSTPPDHGNDL
651  KGYFCHQCFTDQKGERILVEGVSIKKSDLVKRKNDEEIEEGWVQCDHCEG
701  WVHQICGMFNKGRNNTDVHYLCPDCLAVGYERGQRQKTEVRPQAMLEAKD
751  LPTSRLSEFITERLNRELEKEHHKRAEQQGKPLHEVAKPEPLTVRMINSV
801  MKKCEVKPRFHETFGPTDGYPGEFGYRQKVLLLFQSLDGVDVCLFCMYVQ
```

```
 851  EYGKDCPAPNTNVVYLSYLDSVKYFRPEIPSALGPAVSLRTFVYHQLLIA
 901  YVEFTRNMGFEQMYIWACPPMQGDDYILYCHPTKQKTPRSDRLRMWYIEM
 951  LKLAKEEGIVKHLSTLWDTYFEGGRDHRMERCSVTYIPYMEGDYWPGEAE
1001  NQLMAINDAAKGKPGTKGAGSAPSRKAGAKGKRYGGGPATADEQLMARLG
1051  EILGGNMREDFIVVHMQVPCTFCRAHIRGPNVVYRYRTPPGATPPKAAPE
1101  RKFEGIKLEGGGPSVPVGTVSSLTICEACFRDEETRTLTGQQLRLPAGVS
1151  TAELAMEKLEEMIQWDRDPDGDMESEFFETRQTFLSLCQGNHYQFDTLRR
1201  AKHSSMMVLYHLHNPHSPAFASSCNQCNAEIEPGSGFRCTVCPDFDMCAS
1251  CKVNPHKRALDETRQRLTEAERRERNEQLQKTLALLVHACGCHNSACGSN
1301  SCRKVKQLFQHAVHCQSKVTGGCQLCKKMWCLLNLHAKSCTRADCPVPRC
1351  KELKELRRRQTNRQEEKRRAAYAAMLRNQMAGSQAPRPM*.
```

LexA-p300 HAT domain DNA (SEQ ID NO 3) is a nucleic acid sequence corresponding to a gene encoding the LexA binding domain-acetyl-transferase (HAT) domain of the Chlamy p300 protein. Similarly, the LexA binding domain is the sequence up to and including nucleotide 690 and the p300 HAT domain sequence begins at nucleotide 700. A 3-amino acid peptide linker (GVL) connects LexA binding domain and p300, which represents the DNA restriction site PpuMI (9 bp).

```
                                                SEQ ID NO 3
   1  ATGAAGGCTCTCACCGCTCGCCAACAGGAGGTCTTTGATCTGATTCGCGA
  51  CCACATCTCGCAGACCGGCATGCCGCCGACCCGGGCGGAGATTGCTCAGC
 101  GGCTGGGCTTCCGGAGCCCCAACGCGGCCGAGGAGCACCTGAAGGCCCTC
 151  GCGCGCAAGGGGGTGATCGAGATTGTCTCCGGCGCTAGCCGCGGCATCCG
 201  CCTGCTGCAGGAGGAGGAGGAGGGCCTGCCGCTGGTCGGGCGGGTCGCGG
 251  CCGGGGAGCCTCTGCTGGCCCAGCAGCACATCGAGGGCCACTACCAAGTG
 301  GACCCCTCGCTGTTTAAGCCCAACGCGGACTTCCTGCTCCGGGTGTCGGG
 351  CATGAGCATGAAGGACATCGGCATCATGGACGGCGACCTCCTGGCGGTGC
 401  ACAAGACCCAGGACGTGCGCAACGGCCAGGTGGTCGTCGCGCGGATTGAC
 451  GACGAGGTGACCGTGAAGCGGCTGAAGAAGCAGGGCAACAAGGTCGAGCT
 501  GCTGCCCGAGAACTCGGAGTTCAAGCCTATCGTGGTCGACCTGCGCCAGC
 551  AGTCCTTCACCATCGAGGGCCTGGCCGTGGGGGTCATCCGCAACGGTGAC
 601  TGGCTGGAGTTCCCCGGCATCCGGCGCCCGTGGCGGCCGCTGGAGTCCAC
 651  CTGCAGCCAGGCGAACTCCGGCCGCATCTCCTACGATCTGGGGGTCCTTG
 701  AGGTGGCCAAGCCGGAGCCGCTGACCGTGCGGATGATCAACAGCGTGATG
 751  AAGAAGTGCGAGGTCAAGCCCCGCTTCCACGAGACGTTCGGTCCGACCGA
 801  CGGTTACCCCGGGGAGTTCGGCTACCGGCAGAAGGTGCTCCTCCTGTTCC
 851  AGTCCCTCGACGGCGTCGACGTGTGCCTGTTCTGCATGTACGTGCAGGAG
 901  TACGGGAAGGACTGCCCGGCGCCCAACACGAACGTGGTGTACCTGAGCTA
 951  CCTGGACTCCGTCAAGTATTTCCGCCCCGAGATTCCCAGCGCCCTGGGCC
1001  CTGCGGTGAGCCTGCGGACCTTCGTGTACCACCAGCTCCTGATTGCGTAC
1051  GTGGAGTTCACGCGCAACATGGGCTTCGAGCAGATGTACATTTGGGCGTG
1101  CCCCCCCATGCAGGGGGACGACTATATCCTGTATTGCCATCCCACGAAGC
1151  AGAAGACCCCGCGCTCGGACCGCCTGCGCATGTGGTACATCGAGATGCTG
1201  AAGCTGGCTAAGGAGGAGGGCATCGTGAAGCACCTGTCGACGCTGTGGGA
```

```
1251 CACCTACTTCGAGGGCGGTCGCGACCACCGGATGGAGCGCTGCAGCGTGA

1301 CCTACATCCCCTACATGGAGGGCGACTACTGGCCTGGCGAGGCCGAGTAA.
```

LexA-p300 HAT domain AA (SEQ ID NO 4) is an exemplary GEE protein sequence of a LexA binding domain-Chlamy p300 protein, where the Chlamy p300 is limited to the histone acetyl-transferase (HAT) domain of the Chlamy p300 enzyme. The LexA binding domain is the sequence up to and including amino acid 230 and the p300 HAT domain sequence begins at amino acid 234. The 3-amino acid peptide linker (GVL) connects LexA binding domain and p300:

```
                                                SEQ ID NO 4
  1 MKALTARQQEVFDLIRDHISQTGMPPTRAEIAQRLGFRSPNAAEEHLKAL
 51 ARKGVIEIVSGASRGIRLLQEEEEGLPLVGRVAAGEPLLAQQHIEGHYQV
101 DPSLFKPNADFLLRVSGMSMKDIGIMDGDLLAVHKTQDVRNGQVVVARID
151 DEVTVKRLKKQGNKVELLPENSEFKPIVVDLRQQSFTIEGLAVGVIRNGD
201 WLEFPGIRRPWRPLESTCSQANSGRISYDLGVLEVAKPEPLTVRMINSVM
251 KKCEVKPRFHETFGPTDGYPGEFGYRQKVLLLFQSLDGVDVCLFCMYVQE
301 YGKDCPAPNTNVVYLSYLDSVKYFRPEIPSALGPAVSLRTFVYHQLLIAY
351 VEFTRNMGFEQMYIWACPPMQGDDYILYCHPTKQKTPRSDRLRMWYIEML
401 KLAKEEGIVKHLSTLWDTYFEGGRDHRMERCSVTYIPYMEGDYWPGEAE*.
```

Codon-optimized Venus gene sequence is a preferred embodiment:

```
                                                SEQ ID NO 5
  1 ATGGTGTCGAAGGGTGAGGAGCTGTTTACCGGTGTCGTGCCTATTCTGGT
 51 GGAGCTCGACGGCGACGTCAACGGGCACAAGTTTTCGGTGTCCGGCGAGG
101 GTGAGGGGACGCGACGTACGGCAAGCTCACGCTGAAGCTGATCTGCACC
151 ACCGGCAAGCTGCCCGTCCCCTGGCCGACGCTGGTGACCACCCTGGGCTA
201 CGGCCTGCAGTGCTTCGCCCGCTACCCGGACCACATGAAGCAGCACGACT
251 TCTTCAAGTCGGCCATGCCCGAGGGGTACGTGCAGGAGCGCACGATCTTC
301 TTTAAGGACGATGGCAACTACAAGACCCGCGCTGAGGTGAAGTTCGAGGG
351 CGATACGCTGGTGAACCGCATCGAGCTCAAGGGCATCGACTTCAAGGAGG
401 ACGGCAACATCCTGGGTCACAAGCTGGAGTACAACTACAACTCCCACAAC
451 GTGTACATCACGGCGGATAAGCAGAAGAACGGCATCAAGGCCAACTTTAA
501 GATTCGCCATAACATCGAGGACGGCGGCGTGCAGCTCGCCGACCACTACC
551 AGCAGAACACCCCGATCGGCGACGGCCCCGTGCTGCTGCCCGATAACCAC
601 TACCTCAGCTACCAGTCGGCCCTGTCCAAGGATCCCAACGAGAAGCGCGA
651 TCACATGGTCCTCCTGGAGTTCGTGACCGCCGCTGGCATCACCCTGGGCA
701 TGGACGAGCTGTACAAGTAA.
```

SEQ ID NO 6 is the protein encoded by the nucleic acid of SEQ ID NO 5. The Venus AA sequence:

```
                                                SEQ ID NO 6
  1 MVSKGEELFTGVVPILVELDGDVNGHKFSVSGEGEGDATYGKLTLKLICT
 51 TGKLPVPWPTLVTTLGYGLQCFARYPDHMKQHDFFKSAMPEGYVQERTIF
101 FKDDGNYKTRAEVKFEGDTLVNRIELKGIDFKEDGNILGHKLEYNYNSHN
```

```
151  VYITADKQKNGIKANFKIRHNIEDGGVQLADHYQQNTPIGDGPVLLPDNH

201  YLSYQSALSKDPNEKRDHMVLLEFVTAAGITLGMDELYK*.
```

SEQ ID NO 7 is a nucleic acid encoding a Venus-Bcl-$x_L$ fusion of the invention. It was designed to represent preferred codon usage in algae. The sequence up to and including nucleotide 717 represents Venus. A 3-amino acid peptide linker (GVL) connects Venus and Bcl-$x_L$, which represents the DNA restriction site PpuMI (9 bp). Bcl-$x_L$ begins at nucleotide 726.

```
                                                    SEQ ID NO 7
   1  ATGGTGTCGAAGGGTGAGGAGCTGTTTACCGGTGTCGTGCCTATTCTGGT

51  GGAGCTCGACGGCGACGTCAACGGGCACAAGTTTTCGGTGTCCGGCGAGG

101  GTGAGGGGACGCGACGTACGGCAAGCTCACGCTGAAGCTGATCTGCACC

151  ACCGGCAAGCTGCCCGTCCCCTGGCCGACGCTGGTGACCACCCTGGGCTA

201  CGGCCTGCAGTGCTTCGCCCGCTACCCGGACCACATGAAGCAGCACGACT

251  TCTTCAAGTCGGCCATGCCCGAGGGGTACGTGCAGGAGCGCACGATCTTC

301  TTTAAGGACGATGGCAACTACAAGACCCGCGCTGAGGTGAAGTTCGAGGG

351  CGATACGCTGGTGAACCGCATCGAGCTCAAGGGCATCGACTTCAAGGAGG

401  ACGGCAACATCCTGGGTCACAAGCTGGAGTACAACTACAACTCCCACAAC

451  GTGTACATCACGGCGGATAAGCAGAAGAACGGCATCAAGGCCAACTTTAA

501  GATTCGCCATAACATCGAGGACGGCGGCGTGCAGCTCGCCGACCACTACC

551  AGCAGAACACCCCGATCGGCGACGGCCCCGTGCTGCTGCCCGATAACCAC

601  TACCTCAGCTACCAGTCGGCCCTGTCCAAGGATCCCAACGAGAAGCGCGA

651  TCACATGGTCCTCCTGGAGTTCGTGACCGCCGCTGGCATCACCCTGGGCA

701  TGGACGAGCTGTACAAGGGGGTCCTTATGAGCCAGAGCAACCGGGAGCTG

751  GTGGTGGACTTCCTGAGCTACAAGCTGAGCCAAAAGGGCTATAGCTGGTC

801  GCAGTTCTCCGACGTCGAGGAGAACCGGACCGAGGCCCCCGAGGGGACCG

851  AGTCCGAGATGGAGACGCCGAGCGCGATTAACGGCAACCCGAGCTGGCAC

901  CTGGCGGACTCCCCTGCCGTGAACGGCGCGACCGGCCACAGCTCCAGCCT

951  GGACGCGCGCGAGGTCATCCCGATGGCGGCCGTGAAGCAGGCCCTCCGCG

1001  AGGCCGGCGACGAGTTCGAGCTGCGCTATCGCCGCGCTTTCTCGGACCTG

1051  ACCAGCCAGCTGCACATCACCCCCGGCACGGCTTACCAAAGCTTCGAGCA

1101  GGTGGTGAACGAGCTGTTCCGCGACGGCGTGAACTGGGGTCGCATCGTGG

1151  CGTTCTTCAGCTTCGGCGGTGCGCTGTGCGTGGAGAGCGTCGACAAGGAG

1201  ATGCAGGTGCTGGTGTCGCGCATTGCGGCTTGGATGGCCACCTACCTGAA

1251  CGACCACCTGGAGCCCTGGATTCAGGAGAACGGCGGCTGGGACACCTTCG

1301  TCGAGCTGTACGGCAACAACGCTGCGGCGGAGAGCCGCAAGGGCCAAGAG

1351  CGGTTCAACCGCTGGTTCCTCACGGGGATGACCGTGGCGGGCGTCGTCCT

1401  GCTGGGCAGCCTGTTCTCGCGGAAGTAA.
```

Venus-Bcl-$x_L$ Protein (SEQ ID NO 8) is the protein fusion encoded by the nucleic acid of SEQ ID NO 7. The underlying Bcl-$x_L$ protein sequence (233 AA) is encoded by the DNA sequence GenBank ID: 20336334 from NCBI Database:

It will be recognized by a skilled artisan that other design approaches are available, including the incorporation within the vector of additional or different genes incorporated for expression, different gene expression control features, other

```
                                                    SEQ ID NO 8
  1    MVSKGEELFTGVVPILVELDGDVNGHKFSVSGEGEGDATYGKLTLKLICT

51    TGKLPVPWPTLVTTLGYGLQCFARYPDHMKQHDFFKSAMPEGYVQERTIF

101    FKDDGNYKTRAEVKFEGDTLVNRIELKGIDFKEDGNILGHKLEYNYNSHN

151    VYITADKQKNGIKANFKIRHNIEDGGVQLADHYQQNTPIGDGPVLLPDNH

201    YLSYQSALSKDPNEKRDHMVLLEFVTAAGITLGMDELYKGVLMSQSNREL

251    VVDFLSYKLSQKGYSWSQFSDVEENRTEAPEGTESEMETPSAINGNPSWH

301    LADSPAVNGATGHSSSLDAREVIPMAAVKQALREAGDEFELRYRRAFSDL

351    TSQLHITPGTAYQSFEQVVNELFRDGVNWGRIVAFFSFGGALCVESVDKE

401    MQVLVSRIAAWMATYLNDHLEPWIQENGGWDTFVELYGNNAAAESRKGQE

451    RFNRWFLTGMTVAGVVLLGSLFSRK*.
```

Example 1

An Exemplary Vector of the Invention

FIG. 1 illustrates a construct in accordance to the invention. The starting vector is pSP124. See V. Lumbreras, D. R. S. and S. Purton, Plant J., 14(4):441-447 (1998). Features of the vector are listed in FIG. 1, i.e. the two regions indicated in FIG. 1 to be part of the backbone vector, pSP124.

None pSP124 sequences are preferably engineered as individual synthetic DNA fragments and strung together via restriction enzyme sites, by well-known techniques. Alternative approaches and mixtures of approaches are available. For example, some features are optionally introduced as PCR products or "cut and pasted" from other available constructs. Typically, sequencing and/or other assays (e.g. size analysis, hybridization) are used to verify the resultant vector.

As an example, one section of the insert is created by synthesis of a region having a BamHI site and ending with an EcoRI site ("Synthetic_1"). This region provides a transcriptional enhancer region, two LexA binding motifs, a rubisco transcriptional promoter (including the first intron of rbcS2), a YFP-Bcl-$x_L$ fusion protein, and a rubisco 3'UTR. The YFP and Bcl-$x_L$ coding regions were designed in this instance to reflect the preferred codon usage in algae.

Another region incorporated is prepared by high fidelity PCR and effectively provides the p300 (HAT) gene ("Genomic PCR"). Flanking the genomic PCR fragment are two additional regions prepared by synthetic DNA ("Synthetic_2"). The region transcriptionally upstream of the p300 gene provides the LexA binding domain coding sequence downstream of transcriptional promoters and two LexA binding sites. The Synthetic_2 region provides a 3'UTR. Combined, the Synthetic_2 and Genomic regions create a complete transcription unit encoding a LexA-p300 fusion protein (GEE).

Effectively, FIG. 1 and these explanations provide an example of the features of a construct of the invention and illustrate methods of creating the features within an algae compatible plasmid. Two transcriptional units face opposing directions and each have two LexA binding sites, creating an opportunity for the LexA-p300 to bind at any of four sites and affect transcription levels of either transcriptional unit. A third transcriptional unit provides a selection marker, bleomycin-resistance.

restriction sites, change the number of LexA-BS, and so on, without changing the concept behind the creation of this vector, namely to effectively increase the levels of expression of the genes located in vicinity of a DNA-BS, in the presence of a GEE that recognizes/binds the BS.

Example 2

Additional Exemplary Vectors

Two vectors are constructed which are in most respects identical, but for the presence of a GEE unit. The vectors are otherwise the same to each other and similar to the vector of FIG. 2A. The use of these vectors in parallel allows testing of the p300 activity and the role of LexA in otherwise identical genetic backgrounds. The use of two vectors also allows for modulation of the GEE activities by such additional engineering, for example, as addition of other genes, addition of multiple copies of GEE and so on.

Notably, "LexA BS" does not refer to any limit of the number of binding sites; anything from one BS to many BS are possibly located at the indicated position. Practically speaking, it is unlikely to utilize more than about 8 BS, as benefit from additional sites would be unlikely. Preferably, about 2 to 6 BS are located in the region at or near the 5'end of genes desirably expressed, more preferably there are 2-4 BS.

Example 3

Characterization of GEE Efficacy with a Bidirectional Promoter

Experiment 1. Use the bidirectional construct with YFP reporter in the position of the GOI and either one of two variants of the GEE construct: [1] in which the LexA-p300 chimeric gene is driven in the opposite direction (FIG. 1) or [2] in which only LexA is driven in the opposite direction which serves as a control.

Algae are transformed with the two constructs and selected on appropriate antibiotic containing selection media (e.g. media containing bleocin). After selection, 100 colonies from transformation for each construct are chosen to analyze the expression of the YFP transgene by assaying mRNA expression using rtPCR, protein expression with Western blot, and single cell fluorescence by flow cytometry and fluorescent microscopy. The clonal populations are passed for 2, 4, 6, and 10 generations. The frequency of high-level expression of YFP are compared between the LexA-p300 and LexA only clones. The LexA-p300 GEE increases expression and maintains a higher level of nuclear transgene expression over time.

Example 4

Characterization of GEE Efficacy Using Distinct Plasmids

Figure 2B:
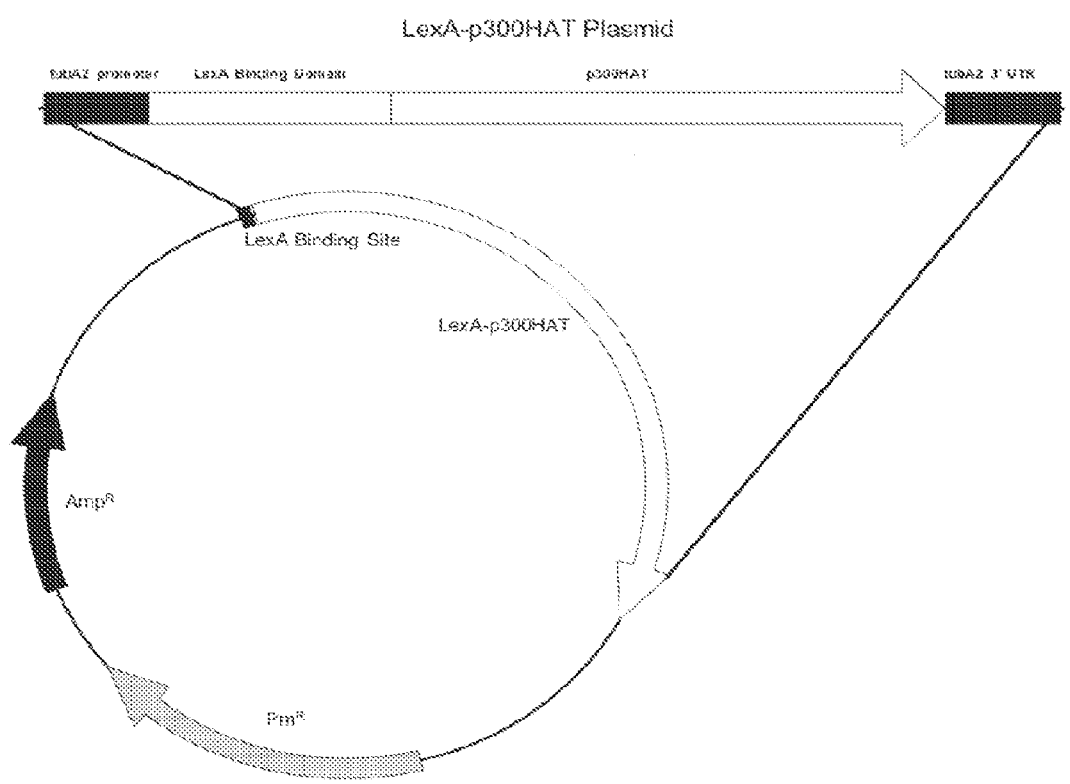

Generate two sets of stable clones: Set one is a stable cell line with the incorporated transgene encoding the LexA-p300 fusion (FIG. 2A) that is then transformed with a plasmid that expresses the YFP vector (FIG. 2B). Set two is a stable cell line with the incorporated transgene encoding the LexA only (related to FIG. 2A with the exception of the p300 fusion partner) that is then transformed with a plasmid that expresses the YFP vector (FIG. 2B).

Select for stable cell lines and characterize the YFP expression over time by assaying mRNA expression by rtPCR, western blot to determine protein expression, and assay of single cell fluorescence by flow cytometry and fluorescent microscopy. The clonal populations will be passaged for 2, 4, 6, and 10 generations. Similarly, the frequency of high-level expression of YFP are compared between the LexA-p300 and LexA only clones. The LexA-p300 GEE increases expression and maintains a higher level of nuclear transgene expression over time.

The invention described above should be read in conjunction with the accompanying claims and drawings. The description of embodiments and examples enable one to practice various implementations of the invention and they are not intended to limit the invention to the preferred embodiment, but to serve as a particular example of the invention. Those skilled in the art will appreciate that they may readily use the conception and specific embodiments disclosed as a basis for modifying or designing other methods and systems for carrying out the same purposes of the present invention.

All references, including publications, patent applications, patents, and website content cited herein are hereby incorporated by reference to the same extent as if each reference were individually and specifically indicated to be incorporated by reference and was set forth in its entirety herein.

The websites mentioned herein were last visited on Oct. 30, 2010.

The use of the terms "a" and "an" and "the" and similar references in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. NO language in the specification should be construed as indicating any non-claimed element as essential to the practice of the invention.

What is claimed is:

1. A eukaryotic unicellular algae, comprising:
a construct for enhanced gene expression in an alga cell, wherein said construct further comprises
a eukaryotic unicellular algae compatible transcriptional promoter functionally upstream of a coding sequence for a gene expression enhancer (GEE) fusion protein, wherein the fusion protein comprises an algae derived p300 functionally fused to the DNA binding protein, wherein at least the portion of the coding sequence of the DNA binding protein domain is codon optimized for improved expression in a eukaryotic unicellular algae;
at least one transgene functionally downstream of a eukaryotic unicellular algae compatible transcriptional promoter; and
at least one DNA region that is a binding site for the DNA binding protein, in vicinity of at least one of said transcriptional promoters.

2. The eukaryotic unicellular algae of claim 1, wherein the DNA binding protein is LexA DNA Binding domain.

3. The eukaryotic unicellular algae of claim 1, wherein the p300 part of the GEE fusion protein is from *Chlamydomonas reinhardtii*.

4. The eukaryotic unicellular algae of claim 1, wherein only a HAT domain of the p300 protein is part of the GEE fusion protein.

5. The eukaryotic unicellular algae of claim 1, wherein the transgene is codon modified for improved expression in algae.

6. The eukaryotic unicellular algae of claim 5, wherein the transgene is a fluorescence-Bcl-$x_L$ fusion gene.

7. The eukaryotic unicellular algae of claim 6, wherein the fluorescence-Bcl-$x_L$ fusion gene is a YFP-Bcl-$x_L$ fusion.

8. The eukaryotic unicellular algae of claim 6, wherein the fluorescence-Bcl-$x_L$ fusion gene is a Venus-Bcl-$x_L$ fusion.

9. The eukaryotic unicellular algae of claim 1, further comprising at least one selective marker.

10. The eukaryotic unicellular algae of claim 9, wherein the GEE fusion protein and the at least one transgene are introduced into the system on one vector and structurally arranged to be expressed from one bidirectional promoter region and comprising DNA binding sites in the vicinity of both promoters.

11. The eukaryotic unicellular algae of claim 9, wherein the GEE fusion protein and the transgene are introduced in the system on separate vectors, each comprising a selective marker and the selective markers are not the same.

12. The eukaryotic unicellular algae of claim 1, wherein the algae compatible transcriptional promoters are hsp70, rbcS, nitA, tubA2 or a combination thereof.

13. The eukaryotic unicellular algae of claim 1, wherein the GEE fusion protein comprises a DNA binding domain functionally fused to an algae derived p300 homologue having at least 80% identity over the HAT region to the p300 from *Chlamydomonas reinhardtii*.

14. The eukaryotic unicellular algae of claim 13, wherein the GEE fusion protein comprises a DNA binding domain functionally fused to the HAT domain from an algae derived p300 homologue, the homologue having at least 80% identity over the HAT region to the p300 from *Chlamydomonas reinhardtii*.

* * * * *

SEQUENCE LISTING

```
<160> NUMBER OF SEQ ID NOS: 9

<210> SEQ ID NO 1
<211> LENGTH: 4170
<212> TYPE: DNA
<213> ORGANISM: Artificial Sequence
<220> FEATURE:
<223> OTHER INFORMATION: LexA-p300 Fusion

<400> SEQUENCE: 1
atgaaggctc tgaccgctcg ccagcaggag gtgtttgatc tgattcggga ccatatcagc      60
caaacgggca tgccccctac gcgcgcggag atcgcgcaac ggctgggctt ccgctcccg     120 aacgcggctg aggagcacct gaaggcgctg gcgcgcaagg gtgtgattga gatcgtctcc     180
ggcgcgtcgc ggggcattcg gctgctgcag gaggaggagg agggtctgcc tctggtgggg     240
cgggtggctg cgggcgagcc cctgctggcc cagcagcaca ttgagggcca ctaccaagtg     300
gacccgtccc tcttcaagcc gaacgccgat ttcctgctgc gcgtcagcgg tatgagcatg     360
aaggacatcg gcatcatgga cggtgacctg ctggccgtgc ataagacgca ggacgtgcgc     420
aacggccaag tggtcgtcgc ccgcatcgat gacgaggtga ccgtgaagcg cctgaagaag     480
caggggaaca aggtcgagct gctgcccgag aacagcgagt tcaagcccat cgtggtggat     540
ctgcgccagc aatccttcac catcgagggc ctggcggtgg gcgtgatccg caacggcgac     600
tggctggagt tcccgggcat ccgccgcccg tggcgccctc tggagtccac gtgctcgcag     660
gccaactccg gccgcattag ctacgacctg ggggtcctta tggtgccgat gggcgcgccc     720
gctatgccca tgggcaacaa cggctcgccc atgctgaacg gcatgggtat gttcaacgcc     780
```

```
ccgcagcaga ccgtgcccaa cggcgggccg ggtggcgtga accccatggg ccaggtgccg    840
gcgatgcctg cgccgatccc caacggcggt ctgcccggta tgaacgctgc cggcggtgcc    900
gacgatcctg cgaagcagcg ggagcaatcg atccagaagc agcagcgctg gctgctgttc    960
ctgcggcact cgcgcaagtg ccgggctccc ggcgaggact ccagctgaa gtcccagtgc    1020
aagttcggca agcagctgtg gcagcacatc ctgtcgtgcc aaaacccggc ctgcgagtac   1080
ccgcgctgca ccaactccaa ggatctgctc aagcaccacc agaagtgcca ggagcagacc   1140
tgccccgtgt gcatgccggt gaaggactac gtgaagaaga cgcgccaggc gacccaacag   1200
cagcaacaaa tgcagcaaca acagcaaatc cagcaacagc aacaacaaca aatgcaacag   1260
caacagatgc aacagcagca gctccagcag cagcagatgc aacaacaaca gcagatgcag   1320
cagcagcaac agcccggcgt gggcgccaac ttcatgccca ccccgcccat gatgccgaac   1380
ggcatgttcc ctcaacagca gccccagcag gcgatgcgcc tgaacgccaa cggcctcggc   1440
ggccagaagc gcccccacga gatgatgggt atgtccagcg gcggcatgga cggtatgaac   1500
cagatggtgc ccgtcggcgg cggcggcatg ggcatgtcga tgccgatggg tatgaacaac   1560
cccatgcagg gcggtatgcc cctgcagcct ccgccccagg tgcaggctcc cggtcagggc   1620
cccatgatga gcgcccctca gcagcaacag cagcaaccgg ccctaagcg ggcgaagacc    1680
gacgatgtgt gcgccagaa cacgggcacc agcctcctgg agacgttcga cgccaagcag   1740
atccgcgtgc acgtggacct gatccgcgct gccgcggtga cccagaaggc ccagcagcct   1800
cccccggcta ccccgacga cgcgtgcaag gtctgcgcgc tgacgaagct gtcgttcgag    1860
cccccggtga tttactgctc gagctgcggc ctgcgcatca gcgcgggcca gatcttctac   1920
agcacgcctc cggaccacgg caacgactg aagggttact tctgccacca gtgcttcacc    1980
gaccagaagg gcgagcgcat cctggtggag ggcgtctcga tcaagaagag cgacctggtg   2040
aagcgcaaga cgatgagga gatcgaggag gggtgggtgc agtgcgacca ctgcgagggc   2100
tgggtgcacc agatttgcgg catgttcaac aagggccgga caacacgga cgtccactac    2160
ctgtgccctg actgcctggc cgtgggctac gagcgcggcc agcgccagaa gacgaggtc    2220
cgccccagg cgatgctcga ggcgaaggat ctgcccacgt cccggctgtc cgagtttatt    2280
acggagcgcc tgaaccgcga gctggagaag gagcaccaca gcgggctga gcagcagggc   2340
aagccgctgc acgaggtggc gaagcccgag cccctgaccg tgcggatgat caactccgtg   2400
atgaagaagt gcgaggtcaa gccgcgcttc cacgagacgt tcggccccac cgacggctac   2460
cccgggagt tcggctaccg gcagaaggtg ctgctgctgt tccaaagcct ggacggtgtc    2520
gacgtgtgcc tgttctgcat gtacgtgcag gagtacggca aggactgccc tgcgcccaac   2580
accaacgtgt gtacctgtc gtatctggac tccgtcaagt acttccgccc tgagattccc    2640
tcggccctgg gcctgccgt gtcgctgcgc accttcgtgt accaccaact cctgatcgcc    2700
tacgtggagt ttacccgcaa catgggtttt gagcagatgt acatttgggc gtgcccgccg    2760
atgcaaggcg acgactacat cctgtactgc cacccgacca gcagaagac gccgcgctcg   2820
gaccgcctgc gcatgtggta cattgagatg ctgaagctgg cgaaggagga gggtatcgtg   2880
aagcacctga gcacgctgtg ggatacgtac ttcgagggcg tcgcgaccac ccggatggag   2940
cgctgctcgg tcacgtacat tccgtacatg gagggcgact actggcccgg cgaggctgag   3000
aaccagctca tggccattaa cgacgcgcc aagggcaagc ctgggaccaa gggtgcgggc   3060
agcgccccga gccgcaaggc cggtgccaag ggcaagcgct acggcggtgg ccccgccacg   3120
```

-continued

```
gctgatgagc agctgatggc ccgcctcggt gagatcctgg gcgggaacat gcgggaggac    3180
ttcattgtgg tccacatgca ggtgccctgc acgttctgcc gcgctcacat tcggggtccg    3240
aacgtggtgt accgctatcg gacgccgcct ggcgcgaccc ctcccaaggc tgccccgag    3300
cgcaagttcg agggcatcaa gctggagggc ggtggcccca gcgtgcccgt gggcaccgtc    3360
tcgagcctga cgatctgcga ggcgtgcttt cgcgacgagg agacgcgcac gctgaccggc    3420
caacagctgc gcctgcccgc tggcgtgtcg accgctgagc tcgcgatgga gaagctggag    3480
gagatgatcc agtgggaccg cgaccctgac ggcgacatgg agagcgagtt cttcgagacg    3540
cggcagacct tcctgtcgct gtgccagggc aaccactacc agttcgacac cctccgccgc    3600
gctaagcact cgtcgatgat ggtgctctac cacctgcaca ccccactc gccggcgttc    3660
gcgtcctcgt gcaaccagtg caacgccgag atcgagccgg gcagcggctt tcgctgcacc    3720
gtgtgccccg acttcgacat gtgcgccagc tgcaaggtca accctcataa gcgcgccctg    3780
gacgagacgc gccagcggct gaccgaggcc gagcgccggg agcgcaacga gcagctgcag    3840
aagaccctcg ccctgctggt gcacgcctgc ggctgccaca cagcgcgtg cggctccaac    3900
agctgccgca aggtgaagca gctgttccag cacgcggtcc actgccagag caaggtgacc    3960
gggggctgcc agctgtgcaa gaagatgtgg tgcctgctga acctgcacgc caagtcctgc    4020
acccgcgcgg actgcccggt gccgcgctgc aaggagctga aggagctgcg ccggcgccaa    4080
acgaaccggc aggaggagaa gcgccgggcg gcctacgccg ctatgctgcg caaccagatg    4140
gccggcagcc aggctccgcg ccccatgtaa                                     4170
```

<210> SEQ ID NO 2
<211> LENGTH: 1389
<212> TYPE: PRT
<213> ORGANISM: Artificial Sequence
<220> FEATURE:
<223> OTHER INFORMATION: LexA-p300 Fusion

<400> SEQUENCE: 2

```
Met Lys Ala Leu Thr Ala Arg Gln Gln Glu Val Phe Asp Leu Ile Arg
  1               5                  10                  15

Asp His Ile Ser Gln Thr Gly Met Pro Pro Thr Arg Ala Glu Ile Ala
             20                  25                  30

Gln Arg Leu Gly Phe Arg Ser Pro Asn Ala Ala Glu Glu His Leu Lys
         35                  40                  45

Ala Leu Ala Arg Lys Gly Val Ile Glu Ile Val Ser Gly Ala Ser Arg
     50                  55                  60

Gly Ile Arg Leu Leu Gln Glu Glu Glu Glu Gly Leu Pro Leu Val Gly
 65                  70                  75                  80

Arg Val Ala Ala Gly Glu Pro Leu Leu Ala Gln Gln His Ile Glu Gly
                 85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175
```

-continued

```
Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
        195                 200                 205

Arg Pro Trp Arg Pro Leu Glu Ser Thr Cys Ser Gln Ala Asn Ser Gly
    210                 215                 220

Arg Ile Ser Tyr Asp Leu Gly Val Leu Met Val Pro Met Gly Ala Pro
225                 230                 235                 240

Ala Met Pro Met Gly Asn Asn Gly Ser Pro Met Leu Asn Gly Met Gly
                245                 250                 255

Met Phe Asn Ala Pro Gln Gln Thr Val Pro Asn Gly Gly Pro Gly Gly
            260                 265                 270

Val Asn Pro Met Gly Gln Val Pro Ala Met Pro Ala Pro Ile Pro Asn
        275                 280                 285

Gly Gly Leu Pro Gly Met Asn Ala Ala Gly Gly Ala Asp Asp Pro Ala
    290                 295                 300

Lys Gln Arg Glu Gln Ser Ile Gln Lys Gln Gln Arg Trp Leu Leu Phe
305                 310                 315                 320

Leu Arg His Cys Ala Lys Cys Arg Ala Pro Gly Glu Asp Cys Gln Leu
                325                 330                 335

Lys Ser Gln Cys Lys Phe Gly Lys Gln Leu Trp Gln His Ile Leu Ser
            340                 345                 350

Cys Gln Asn Pro Ala Cys Glu Tyr Pro Arg Cys Thr Asn Ser Lys Asp
        355                 360                 365

Leu Leu Lys His His Gln Lys Cys Gln Glu Thr Cys Pro Val Cys
    370                 375                 380

Met Pro Val Lys Asp Tyr Val Lys Lys Thr Arg Gln Ala Thr Gln Gln
385                 390                 395                 400

Gln Gln Gln Met Gln Gln Gln Gln Ile Gln Gln Gln Gln Gln Gln Gln
                405                 410                 415

Gln Met Gln Gln Gln Gln Met Gln Gln Gln Leu Gln Gln Gln Gln Gln
            420                 425                 430

Met Gln Gln Gln Gln Gln Met Gln Gln Gln Gln Pro Gly Val Gly
        435                 440                 445

Ala Asn Phe Met Pro Thr Pro Pro Met Met Pro Asn Gly Met Phe Pro
450                 455                 460

Gln Gln Gln Pro Gln Gln Ala Met Arg Leu Asn Ala Asn Gly Leu Gly
465                 470                 475                 480

Gly Gln Lys Arg Pro His Glu Met Met Gly Met Ser Ser Gly Gly Met
                485                 490                 495

Asp Gly Met Asn Gln Met Val Pro Val Gly Gly Gly Met Gly Met
            500                 505                 510

Ser Met Pro Met Gly Met Asn Asn Pro Met Gln Gly Met Pro Leu
        515                 520                 525

Gln Pro Pro Pro Gln Val Gln Ala Pro Gly Gln Gly Pro Met Met Ser
    530                 535                 540

Ala Pro Gln Gln Gln Gln Gln Pro Ala Pro Lys Arg Ala Lys Thr
545                 550                 555                 560

Asp Asp Val Leu Arg Gln Asn Thr Gly Thr Ser Leu Leu Glu Thr Phe
                565                 570                 575

Asp Ala Lys Gln Ile Arg Val His Val Asp Leu Ile Arg Ala Ala
            580                 585                 590

Val Thr Gln Lys Ala Gln Gln Pro Pro Ala Asn Pro Asp Asp Ala
```

-continued

```
             595                 600                 605
Cys Lys Val Cys Ala Leu Thr Lys Leu Ser Phe Glu Pro Pro Val Ile
             610                 615                 620
Tyr Cys Ser Ser Cys Gly Leu Arg Ile Lys Arg Gly Gln Ile Phe Tyr
625                 630                 635                 640
Ser Thr Pro Pro Asp His Gly Asn Asp Leu Lys Gly Tyr Phe Cys His
             645                 650                 655
Gln Cys Phe Thr Asp Gln Lys Gly Glu Arg Ile Leu Val Glu Gly Val
             660                 665                 670
Ser Ile Lys Lys Ser Asp Leu Val Lys Arg Lys Asn Asp Glu Glu Ile
             675                 680                 685
Glu Glu Gly Trp Val Gln Cys Asp His Cys Glu Gly Trp Val His Gln
             690                 695                 700
Ile Cys Gly Met Phe Asn Lys Gly Arg Asn Asn Thr Ala Val His Tyr
705                 710                 715                 720
Leu Cys Pro Asp Cys Leu Ala Val Gly Tyr Glu Arg Gly Gln Arg Gln
             725                 730                 735
Lys Thr Glu Val Arg Pro Gln Ala Met Leu Glu Ala Lys Asp Leu Pro
             740                 745                 750
Thr Ser Arg Leu Ser Glu Phe Ile Thr Glu Arg Leu Asn Arg Glu Leu
             755                 760                 765
Glu Lys Glu His His Lys Arg Ala Glu Gln Gly Lys Pro Leu His
             770                 775                 780
Glu Val Ala Lys Pro Glu Pro Leu Thr Val Arg Met Ile Asn Ser Val
785                 790                 795                 800
Met Lys Lys Cys Glu Val Lys Pro Arg Phe His Glu Thr Phe Gly Pro
             805                 810                 815
Thr Asp Gly Tyr Pro Gly Glu Phe Gly Tyr Arg Gln Lys Val Leu Leu
             820                 825                 830
Leu Phe Gln Ser Leu Asp Gly Val Asp Val Cys Leu Phe Cys Met Tyr
             835                 840                 845
Val Gln Glu Tyr Gly Lys Asp Cys Pro Ala Pro Asn Thr Asn Val Val
             850                 855                 860
Tyr Leu Ser Tyr Leu Asp Ser Val Lys Tyr Phe Arg Pro Glu Ile Pro
865                 870                 875                 880
Ser Ala Leu Gly Pro Ala Val Ser Leu Arg Thr Phe Val Tyr His Gln
             885                 890                 895
Leu Leu Ile Ala Tyr Val Glu Phe Thr Arg Asn Met Gly Phe Glu Gln
             900                 905                 910
Met Tyr Ile Trp Ala Cys Pro Pro Met Gln Gly Asp Asp Tyr Ile Leu
             915                 920                 925
Tyr Cys His Pro Thr Lys Gln Lys Thr Pro Arg Ser Asp Arg Leu Arg
             930                 935                 940
Met Trp Tyr Ile Glu Met Leu Lys Leu Ala Lys Glu Glu Gly Ile Val
945                 950                 955                 960
Lys His Leu Ser Thr Leu Trp Asp Thr Tyr Phe Glu Gly Gly Arg Asp
             965                 970                 975
His Arg Met Glu Arg Cys Ser Val Thr Tyr Ile Pro Tyr Met Glu Gly
             980                 985                 990
Asp Tyr Trp Pro Gly Glu Ala Glu Asn Gln Leu Met Ala Ile Asn Asp
             995                1000                1005
Ala Ala Lys Gly Lys Pro Gly Thr Lys Gly Ala Gly Ser Ala Pro
             1010                1015                1020
```

Ser Arg Lys Ala Gly Ala Lys Gly Lys Arg Tyr Gly Gly Gly Pro
1025            1030            1035

Ala Thr Ala Asp Glu Gln Leu Met Ala Arg Leu Gly Glu Ile Leu
1040            1045            1050

Gly Gly Asn Met Arg Glu Asp Phe Ile Val Val His Met Gln Val
1055            1060            1065

Pro Cys Thr Phe Cys Arg Ala His Ile Arg Gly Pro Asn Val Val
1070            1075            1080

Tyr Arg Tyr Arg Thr Pro Pro Gly Ala Thr Pro Pro Lys Ala Ala
1085            1090            1095

Pro Glu Arg Lys Phe Glu Gly Ile Lys Leu Glu Gly Gly Gly Pro
1100            1105            1110

Ser Val Pro Val Gly Thr Val Ser Ser Leu Thr Ile Cys Glu Ala
1115            1120            1125

Cys Phe Arg Asp Glu Glu Thr Arg Thr Leu Thr Gly Gln Gln Leu
1130            1135            1140

Arg Leu Pro Ala Gly Val Ser Thr Ala Glu Leu Ala Met Glu Lys
1145            1150            1155

Leu Glu Glu Met Ile Gln Trp Asp Arg Asp Pro Asp Gly Asp Met
1160            1165            1170

Glu Ser Glu Phe Phe Glu Thr Arg Gln Thr Phe Leu Ser Leu Cys
1175            1180            1185

Gln Gly Asn His Tyr Gln Phe Asp Thr Leu Arg Arg Ala Lys His
1190            1195            1200

Ser Ser Met Met Val Leu Tyr His Leu His Asn Pro His Ser Pro
1205            1210            1215

Ala Phe Ala Ser Ser Cys Asn Gln Cys Asn Ala Glu Ile Glu Pro
1220            1225            1230

Gly Ser Gly Phe Arg Cys Thr Val Cys Pro Asp Phe Asp Met Cys
1235            1240            1245

Ala Ser Cys Lys Val Asn Pro His Lys Arg Ala Leu Asp Glu Thr
1250            1255            1260

Arg Gln Arg Leu Thr Glu Ala Glu Arg Arg Glu Arg Asn Glu Gln
1265            1270            1275

Leu Gln Lys Thr Leu Ala Leu Leu Val His Ala Cys Gly Cys His
1280            1285            1290

Asn Ser Ala Cys Gly Ser Asn Ser Cys Arg Lys Val Lys Gln Leu
1295            1300            1305

Phe Gln His Ala Val His Cys Gln Ser Lys Val Thr Gly Gly Cys
1310            1315            1320

Gln Leu Cys Lys Lys Met Trp Cys Leu Leu Asn Leu His Ala Lys
1325            1330            1335

Ser Cys Thr Arg Ala Asp Cys Pro Val Pro Arg Cys Lys Glu Leu
1340            1345            1350

Lys Glu Leu Arg Arg Arg Gln Thr Asn Arg Gln Glu Glu Lys Arg
1355            1360            1365

Arg Ala Ala Tyr Ala Ala Met Leu Arg Asn Gln Met Ala Gly Ser
1370            1375            1380

Gln Ala Pro Arg Pro Met
1385

<210> SEQ ID NO 3
<211> LENGTH: 1350

```
<212> TYPE: DNA
<213> ORGANISM: Artificial Sequence
<220> FEATURE:
<223> OTHER INFORMATION: LexA-p300 HAT Domain

<400> SEQUENCE: 3
atgaaggctc tcaccgctcg ccaacaggag gtctttgatc tgattcgcga ccacatctcg      60
cagaccggca tgccgccgac ccgggcggag attgctcagc ggctgggctt ccggagcccc     120
aacgcggccg aggagcacct gaaggccctc gcgcgcaagg gggtgatcga gattgtctcc     180
ggcgctagcc gcggcatccg cctgctgcag gaggaggagg agggcctgcc gctggtcggg     240
cgggtcgcgg ccggggagcc tctgctggcc agcagcaca tcgagggcca ctaccaagtg      300 gaccctcgc tgtttaagcc caacgcggac ttcctgctcc gggtgtcggg catgagcatg      360
aaggacatcg gcatcatgga cggcgaccc ctggcggtgc acaagaccca ggacgtgcgc      420
aacggccagg tggtcgtcgc gcggattgac gacgaggtga ccgtgaagcg gctgaagaag     480
cagggcaaca aggtcgagct gctgcccgag aactcggagt tcaagcctat cgtggtcgac     540
ctgcgccagc agtccttcac catcgagggc ctggccgtgg gggtcatccg caacggtgac     600
tggctggagt tccccggcat ccggcgcccg tggcggccgc tggagtccac ctgcagccag     660
gcgaactccg gccgcatctc ctacgatctg ggggtccttg aggtggccaa gccggagccg     720
ctgaccgtgc ggatgatcaa cagcgtgatg aagaagtgcg aggtcaagcc ccgcttccac     780
gagacgttcg gtccgaccga cggttacccc ggggagttcg gctaccggca gaaggtgctc     840
ctcctgttcc agtccctcga cggcgtcgac gtgtgcctgt tctgcatgta cgtgcaggag     900
tacgggaagg actgcccggc gcccaacacg aacgtggtgt acctgagcta cctggactcc     960
gtcaagtatt tccgcccccga gattccccagc gccctgggcc ctgcggtgag cctgcggacc    1020
ttcgtgtacc accagctcct gattgcgtac gtggagttca cgcgcaacat gggcttcgag    1080
cagatgtaca tttgggcgtg ccccccccatg caggggacg actatatcct gtattgccat    1140
cccacgaagc agaagacccc cgcgctcgga cgcctgcgca tgtggtacat cgagatgctg    1200
aagctggcta aggaggaggg catcgtgaag cacctgtcga cgctgtggga cacctacttc    1260
gagggcggtc gcgaccaccg gatggagcgc tgcagcgtga cctacatccc ctacatggag    1320
ggcgactact ggcctggcga ggccgagtaa                                       1350

<210> SEQ ID NO 4
<211> LENGTH: 449
<212> TYPE: PRT
<213> ORGANISM: Artificial Sequence
<220> FEATURE:
<223> OTHER INFORMATION: LexA-p300 HAT Domain

<400> SEQUENCE: 4
```

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly

```
            85                  90                  95
His Tyr Gln Val Asp Pro Ser Leu Phe Lys Pro Asn Ala Asp Phe Leu
                100                 105                 110
Leu Arg Val Ser Gly Met Ser Met Lys Asp Ile Gly Ile Met Asp Gly
            115                 120                 125
Asp Leu Leu Ala Val His Lys Thr Gln Asp Val Arg Asn Gly Gln Val
        130                 135                 140
Val Val Ala Arg Ile Asp Asp Glu Val Thr Val Lys Arg Leu Lys Lys
145                 150                 155                 160
Gln Gly Asn Lys Val Glu Leu Leu Pro Glu Asn Ser Glu Phe Lys Pro
                165                 170                 175
Ile Val Val Asp Leu Arg Gln Gln Ser Phe Thr Ile Glu Gly Leu Ala
                180                 185                 190
Val Gly Val Ile Arg Asn Gly Asp Trp Leu Glu Phe Pro Gly Ile Arg
            195                 200                 205
Arg Pro Trp Arg Pro Leu Glu Ser Thr Cys Ser Gln Ala Asn Ser Gly
        210                 215                 220
Arg Ile Ser Tyr Asp Leu Gly Val Leu Glu Val Ala Lys Pro Glu Pro
225                 230                 235                 240
Leu Thr Val Arg Met Ile Asn Ser Val Met Lys Lys Cys Glu Val Lys
                245                 250                 255
Pro Arg Phe His Glu Thr Phe Gly Pro Thr Asp Gly Tyr Pro Gly Glu
                260                 265                 270
Phe Gly Tyr Arg Gln Lys Val Leu Leu Leu Phe Gln Ser Leu Asp Gly
            275                 280                 285
Val Asp Val Cys Leu Phe Cys Met Tyr Val Gln Glu Tyr Gly Lys Asp
        290                 295                 300
Cys Pro Ala Pro Asn Thr Asn Val Val Tyr Leu Ser Tyr Leu Asp Ser
305                 310                 315                 320
Val Lys Tyr Phe Arg Pro Glu Ile Pro Ser Ala Leu Gly Pro Ala Val
                325                 330                 335
Ser Leu Arg Thr Phe Val Tyr His Gln Leu Leu Ile Ala Tyr Val Glu
            340                 345                 350
Phe Thr Arg Asn Met Gly Phe Glu Gln Met Tyr Ile Trp Ala Cys Pro
        355                 360                 365
Pro Met Gln Gly Asp Asp Tyr Ile Leu Tyr Cys His Pro Thr Lys Gln
    370                 375                 380
Lys Thr Pro Arg Ser Asp Arg Leu Arg Met Trp Tyr Ile Glu Met Leu
385                 390                 395                 400
Lys Leu Ala Lys Glu Glu Gly Ile Val Lys His Leu Ser Thr Leu Trp
                405                 410                 415
Asp Thr Tyr Phe Glu Gly Gly Arg Asp His Arg Met Glu Arg Cys Ser
            420                 425                 430
Val Thr Tyr Ile Pro Tyr Met Glu Gly Asp Tyr Trp Pro Gly Glu Ala
        435                 440                 445
Glu

<210> SEQ ID NO 5
<211> LENGTH: 720
<212> TYPE: DNA
<213> ORGANISM: Artificial Sequence
<220> FEATURE:
<223> OTHER INFORMATION: Codon Optimized Venus Gene Sequence

<400> SEQUENCE: 5
```

```
atggtgtcga agggtgagga gctgtttacc ggtgtcgtgc ctattctggt ggagctcgac       60
ggcgacgtca acgggcacaa gttttcggtg tccggcgagg gtgaggggga cgcgacgtac      120
ggcaagctca cgctgaagct gatctgcacc accggcaagc tgcccgtccc ctggccgacg      180
ctggtgacca ccctgggcta cggcctgcag tgcttcgccc gctacccgga ccacatgaag      240
cagcacgact tcttcaagtc ggccatgccc gaggggtacg tgcaggagcg cacgatcttc      300
tttaaggacg atggcaacta caagacccgc gctgaggtga agttcgaggg cgatacgctg      360
gtgaaccgca tcgagctcaa gggcatcgac ttcaaggagg acggcaacat cctgggtcac      420
aagctggagt acaactacaa ctcccacaac gtgtacatca cggcggataa gcagaagaac      480
ggcatcaagg ccaactttaa gattcgccat aacatcgagg acggcggcgt gcagctcgcc      540
gaccactacc agcagaacac cccgatcggc gacggccccg tgctgctgcc cgataaccac      600
tacctcagct accagtcggc cctgtccaag gatcccaacg agaagcgcga tcacatggtc      660
ctcctggagt tcgtgaccgc cgctggcatc accctgggca tggacgagct gtacaagtaa      720
```

<210> SEQ ID NO 6
<211> LENGTH: 239
<212> TYPE: PRT
<213> ORGANISM: Artificial Sequence
<220> FEATURE:
<223> OTHER INFORMATION: Codon Optimized Venus Sequence

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Ile
            35                  40                  45

Cys Thr Thr Gly Lys Leu Pro Val Pro Trp Pro Thr Leu Val Thr Thr
        50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 7
<211> LENGTH: 1428
<212> TYPE: DNA
<213> ORGANISM: Artificial Sequence
<220> FEATURE:
<223> OTHER INFORMATION: Venus-Bcl-x Fusion

<400> SEQUENCE: 7

```
atggtgtcga agggtgagga gctgtttacc ggtgtcgtgc ctattctggt ggagctcgac      60
ggcgacgtca acgggcacaa gttttcggtg tccggcgagg gtgaggggga cgcgacgtac     120
ggcaagctca cgctgaagct gatctgcacc accggcaagc tgcccgtccc ctggccgacg     180
ctggtgacca cgctgggcta cggcctgcag tgcttcgccc gctacccgga ccacatgaag     240
cagcacgact tcttcaagtc ggccatgccc gaggggtacg tgcaggagcg cacgatcttc     300
tttaaggacg atggcaacta caagacccgc gctgaggtga agttcgaggg cgatacgctg     360
gtgaaccgca tcgagctcaa gggcatcgac ttcaaggagg acggcaacat cctgggtcac     420
aagctggagt acaactacaa ctcccacaac gtgtacatca cggcggataa gcagaagaac     480
ggcatcaagg ccaactttaa gattcgccat aacatcgagg acggcggcgt gcagctcgcc     540
gaccactacc agcagaacac cccgatcggc gacggccccg tgctgctgcc cgataaccac     600
tacctcagct accagtcggc cctgtccaag gatcccaacg agaagcgcga tcacatggtc     660
ctcctggagt tcgtgaccgc cgctggcatc accctgggca tggacgagct gtacaagggg     720
gtccttatga ccagagcaa ccgggagctg gtggtggact cctgagcta caagctgagc     780
caaaagggct atagctggtc gcagttctcc gacgtcgagg agaaccggac cgaggccccc     840
gagggggaccg agtccgagat ggagacgccg agcgcgatta cggcaaccc gagctggcac     900
ctggcggact ccctgccgt gaacggcgcg accggccaca gctccagcct ggacgcgcgc     960
gaggtcatcc cgatggcggc cgtgaagcag gccctccgcg aggccggcga cgagttcgag    1020
ctgcgctatc gccgcgcttt ctcggacctg accagccagc tgcacatcac ccccggcacg    1080
gcttaccaaa gcttcgagca ggtggtgaac gagctgttcc gcgacggcgt gaactggggt    1140
cgcatcgtgg cgttcttcag cttcggcggt gcgctgtgcg tggagagcgt cgacaaggag    1200
atgcaggtgc tggtgtcgcg cattgcggct tggatggcca cctacctgaa cgaccacctg    1260
gagccctgga ttcaggagaa cggcggctgg gacaccttcg tcgagctgta cggcaacaac    1320
gctgcggcgg agagccgcaa gggccaagag cggttcaacc gctggttcct cacggggatg    1380
accgtggcgg gcgtcgtcct gctgggcagc ctgttctcgc ggaagtaa               1428
```

<210> SEQ ID NO 8
<211> LENGTH: 475
<212> TYPE: PRT
<213> ORGANISM: Artificial Sequence
<220> FEATURE:
<223> OTHER INFORMATION: Venus-Bclx Fusion

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
```

```
            50                  55                  60
Leu Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                     85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gly
225                 230                 235                 240

Val Leu Met Ser Gln Ser Asn Arg Glu Leu Val Val Asp Phe Leu Ser
                245                 250                 255

Tyr Lys Leu Ser Gln Lys Gly Tyr Ser Trp Ser Gln Phe Ser Asp Val
            260                 265                 270

Glu Glu Asn Arg Thr Glu Ala Pro Glu Gly Thr Glu Ser Glu Met Glu
        275                 280                 285

Thr Pro Ser Ala Ile Asn Gly Asn Pro Ser Trp His Leu Ala Asp Ser
        290                 295                 300

Pro Ala Val Asn Gly Ala Thr Gly His Ser Ser Ser Leu Asp Ala Arg
305                 310                 315                 320

Glu Val Ile Pro Met Ala Ala Val Lys Gln Ala Leu Arg Glu Ala Gly
                325                 330                 335

Asp Glu Phe Glu Leu Arg Tyr Arg Arg Ala Phe Ser Asp Leu Thr Ser
            340                 345                 350

Gln Leu His Ile Thr Pro Gly Thr Ala Tyr Gln Ser Phe Glu Gln Val
        355                 360                 365

Val Asn Glu Leu Phe Arg Asp Gly Val Asn Trp Gly Arg Ile Val Ala
370                 375                 380

Phe Phe Ser Phe Gly Gly Ala Leu Cys Val Glu Ser Val Asp Lys Glu
385                 390                 395                 400

Met Gln Val Leu Val Ser Arg Ile Ala Ala Trp Met Ala Thr Tyr Leu
                405                 410                 415

Asn Asp His Leu Glu Pro Trp Ile Gln Glu Asn Gly Gly Trp Asp Thr
            420                 425                 430

Phe Val Glu Leu Tyr Gly Asn Asn Ala Ala Ala Glu Ser Arg Lys Gly
        435                 440                 445

Gln Glu Arg Phe Asn Arg Trp Phe Leu Thr Gly Met Thr Val Ala Gly
        450                 455                 460

Val Val Leu Leu Gly Ser Leu Phe Ser Arg Lys
465                 470                 475
```

```
<210> SEQ ID NO 9
<211> LENGTH: 16
<212> TYPE: DNA
<213> ORGANISM: Artificial Sequence
<220> FEATURE:
<223> OTHER INFORMATION: LexA-Binding Site

<400> SEQUENCE: 9
ctgtatatat atacag                                                   16
```